US012579179B2

(12) United States Patent
Yang et al.

(10) Patent No.: US 12,579,179 B2
(45) Date of Patent: Mar. 17, 2026

(54) MACHINE LEARNING TECHNIQUES FOR CLASSIFYING DOCUMENT DATA OBJECTS

(71) Applicant: Optum, Inc., Minnetonka, MN (US)

(72) Inventors: Zhichao Yang, Amherst, MA (US); Joel David Stremmel, Iowa City, IA (US); Sanjit Singh Batra, Redwood City, CA (US); Eran Halperin, Santa Monica, CA (US)

(73) Assignee: Optum, Inc., Minnetonka, MN (US)

( * ) Notice: Subject to any disclaimer, the term of this patent is extended or adjusted under 35 U.S.C. 154(b) by 303 days.

(21) Appl. No.: 18/515,995

(22) Filed: Nov. 21, 2023

(65) Prior Publication Data

US 2025/0068671 A1    Feb. 27, 2025

Related U.S. Application Data

(60) Provisional application No. 63/520,785, filed on Aug. 21, 2023.

(51) Int. Cl.
    *G06F 16/355* (2025.01)
    *G06F 40/289* (2020.01)
    *G16H 50/20* (2018.01)

(52) U.S. Cl.
    CPC .......... *G06F 16/355* (2019.01); *G06F 40/289* (2020.01); *G16H 50/20* (2018.01)

(58) Field of Classification Search
    CPC ............................ G06F 16/355; G06F 40/289
    USPC .................................................. 704/202, 232
    See application file for complete search history.

(56) References Cited

U.S. PATENT DOCUMENTS

| | | | |
|---|---|---|---|
| 9,147,041 B2 | 9/2015 | Amarasingham et al. | |
| 10,395,772 B1 | 8/2019 | Lucas et al. | |
| 11,087,088 B2 | 8/2021 | Chatterjee et al. | |
| 11,314,790 B2 | 4/2022 | Chang et al. | |

(Continued)

FOREIGN PATENT DOCUMENTS

| | | | | |
|---|---|---|---|---|
| CN | 113420151 A | * | 9/2021 | ......... G06F 16/3346 |
| CN | 113535694 A | | 10/2021 | |

(Continued)

OTHER PUBLICATIONS

"Good Machine Learning Practice For Medical Device Development: Guiding Principles," U.S. Food & Drug Administration, Oct. 27, 2021, (2 pages), [Retrieved from the Internet Feb. 7, 2023] <URL: https://www.fda.gov/medical-devices/software-medical-device-samd/good-machine-learning-practice-medical-device-development-guiding-principles>.

(Continued)

*Primary Examiner* — George C Monikang

(74) *Attorney, Agent, or Firm* — Alston & Bird LLP

(57) ABSTRACT

Various embodiments of the present disclosure provide methods, apparatus, systems, computing devices, computing entities, and/or the like for identifying one or more evidence text portions comprising one or more bases relied on by a generative machine learning model for assigning a plurality of model-assigned categorical identifiers to a plurality of text segment data objects associated with a document data object, and verifying the one or more evidence text portions with a verifier machine learning model to generate one or more classifications of the document data object and provide the one or more verified evidence text portions along with the one or more classifications.

20 Claims, 11 Drawing Sheets

(56) References Cited

U.S. PATENT DOCUMENTS

| | | | |
|---|---|---|---|
| 11,791,048 | B2 | 10/2023 | Pang et al. |
| 12,032,921 | B2 | 7/2024 | Peleg et al. |
| 2020/0097713 | A1 | 3/2020 | Cramer et al. |
| 2020/0184016 | A1 | 6/2020 | Roller |
| 2020/0193153 | A1 | 6/2020 | Lee et al. |
| 2020/0279105 | A1 | 9/2020 | Muffat et al. |
| 2020/0411147 | A1 | 12/2020 | Kapit et al. |
| 2021/0216762 | A1 | 7/2021 | Brooks et al. |
| 2021/0224306 | A1 | 7/2021 | Choudhary et al. |
| 2022/0005463 | A1 | 1/2022 | Bender et al. |
| 2022/0083898 | A1 | 3/2022 | Shukla et al. |
| 2022/0114494 | A1 | 4/2022 | Saleiro et al. |
| 2022/0129791 | A1 | 4/2022 | Nia et al. |
| 2022/0351868 | A1 | 11/2022 | Godbole et al. |
| 2023/0222285 | A1 | 7/2023 | Zhang et al. |
| 2023/0334887 | A1 | 10/2023 | Stremmel et al. |
| 2024/0320422 | A1 | 9/2024 | Peleg et al. |

FOREIGN PATENT DOCUMENTS

| | | |
|---|---|---|
| CN | 112418409 B | 8/2023 |
| EP | 3365800 A4 | 2/2019 |
| WO | 2024/042164 A2 | 2/2024 |

OTHER PUBLICATIONS

"Integrated Gradients," Dec. 15, 2022, TensorFlow Core, (25 pages), (online), [Retrieved from the Internet Feb. 7, 2022] <URL: https://www.tensorflow.org/tutorials/interpretability/integrated_gradients>.

Ahmed, Nizar et al. "Classification Of Biomedical Texts For Cardiovascular Diseases With Deep Neural Network Using A Weighted Feature Representation Method," Healthcare, vol. 8, No. 4, pp. 1-15, Oct. 10, 2020, DOI: http://dx.doi.org/10.3390/healthcare8040392.

Arras, Leila et al. "Explaining Predictions of Non-Linear Classifiers in NLP," arXiv PrePrint arXiv: 1606.07298v1 [cs.CL] Jun. 23, 2016 (7 pages), DOI: https://arxiv.org/pdf/1606.07298.pdf.

Cai, Weihong et al. "Multi-Layer Contextual Passage Term Embedding for Ad-Hoc Retrieval," Information, vol. 13, No. 5, pp. 1-16, Apr. 25, 2022, DOI: http://dx.doi.org/10.3390/info13050221.

Dong, Qian et al. "Disentangled Graph Recurrent Network for Document Ranking," Data Science and Engineering, vol. 7, No. 1, pp. 30-43, Feb. 15, 2022, DOI: https://doi.org/10.1007/s41019-022-00179-3.

Huang, et al., "PLM-ICD: Automatic ICD Coding with Pretrained Language Models", Jul. 12, 2022, (12 pages), arXiv:2207.05289v1.

Ji, Shaoxiong et al. "Does The Magic of BERT Apply to Medical Code Assignment? A Quantitative Study," Computers in Biology and Medicine, vol. 139:104998, Oct. 26, 2021, pp. 1-7, available online: https://doi.org/10.1016/j.compbiomed.2021.104998.

Jin, Xisen et al. "Towards Hierarchical Importance Attribution: Explaining Compositional Semantics for Neural Sequence Models," arXiv PrePrint arXiv:1911.06194v1 [cs.CL] Nov. 8, 2019, (12 pages), available online at https://arxiv.org/pdf/1911.06194v1.pdf.

Kokalj, Enja et al. "BERT Meets Shapley: Extending SHAP Explanations to Transformer-Based Classifiers," In Proceedings of The EACL Hackashop on News Media Content Analysis and Automated Report Generation, Apr. 2021, pp. 16-21, available online at https://aclanthology.org/2021.hackashop-1.3.pdf.

Lundberg, Scott. "SHAP: A Game Theoretic Approach to Explain the Output of Any Machine Learning Model," Github, Jun. 15, 2022, (8 pages), [Retrieved from the Internet Feb. 7, 2023] <URL: https://github.com/slundberg/shap>.

Mahbub, Maria et al. "Unstructured Clinical Notes Within The 24 Hours Since Admission Predict Short, Mid & Long-Term Mortality in Adult ICU Patients," PLoS One, vol. 17, No. 1:e0262182, pp. 1-23, Jan. 6, 2022, DOI: https://doi.org/10.1371/journal.pone.0262182.

Mehta, Vivek et al. "WEClustering: Word Embeddings Based Text Clustering Technique for Large Datasets," Complext & Intelligent Systems, vol. 7, pp. 3211-3224, DOI: https://doi.org/10.1007/s40747-021-00512-9.

Pierse, Charles. "Transformers Interpret," Oct. 17, 2022, (3 pages), (online), [Retrieved from the Internet Feb. 7, 2023] <URL: https://github.com/cdpierse/transformers-interpret#sequence-classification-explainer>.

Skrlj, Blaz, et al. "Exploring Neural Language Models via Analysis of Local and Global Self-Attention Spaces," In Proceedings of the EACL Hackashop on News Media Content Analysis and Automated Report Generation, Apr. 19, 2021, pp. 76-83, available online at https://aclanthology.org/2021.hackashop-1.11.pdf.

Sun, Xu et al. "Feature-Frequency-Adaptive On-Line Training for Fast and Accurate Natural Language Processing," Computational Linguistics, vol. 40, No. 3, pp. 563-586, Sep. 1, 2014, DOI: 10.1162/COLL_a_00193.

Sundararajan, Mukund et al. "Axiomatic Attribution For Deep Networks," In Proceedings of the 34th International Conference on Machine Learning, PMLR, vol. 70, pp. 3319-3328, (Year: 2017). PMLR. https://arxiv.org/pdf/1703.01365.

Yin, Kayo et al. "Interpreting Language Models With Contrastive Explanations," arXiv preprint arXiv:2202.10419. https://arxiv.org/pdf/2202.10419v1 [cs.CL] Feb. 21, 2022, (13 pages), available online at https://arxiv.org/pdf/2202.10419v1.pdf.

Zhang, Sheng et al. "Locally Aggregated Feature Attribution on Natural Language Model Understanding," arXiv PrePrint arXiv: 2204.10893v2 [cs.CL] Apr. 26, 2022, (13 pages), DOI: https://arxiv.org/pdf/2204.10893.pdf.

Chalkidis, et al., "An Exploration of Hierarchical Attention Transformers for Efficient Long Document Classification", available online at https://arxiv.org/pdf/2210.05529, Oct. 11, 2022, (16 pages).

Kim, et al., "Feature Attribution Analysis to Quantify the Impact of Oceanographic and Maneuverability Factors on Vessel Shaft Power Using Explainable Tree-Based Model", Sensors, vol. 23, Jan. 17, 2023, (21 pages), DOI:10.3390/s23031072.

Notice of Allowance and Fees Due (PTOL-85) Mailed on Jan. 3, 2025 for U.S. Appl. No. 18/046,831, 15 page(s).

Notice of Allowance and Fees Due (PTOL-85) Mailed on Jan. 15, 2025 for U.S. Appl. No. 18/046,831, 2 page(s).

Rasmy, et al., "Med-BERT: Pretrained Contextualized Embeddings on Largescale Structured Electronic Health Records for Disease Prediction", Digital Medicine vol. 4, No. 86, May 20, 2021, (13 pages), DOI: 10.1038/s41746-021-00455-y.

Sood, et al., "Feature Importance Explanations for Temporal Black-Box Models", available online at https://arxiv.org/pdf/2102.11934.pdf, Feb. 23, 2021, (13 pages).

Stremmel, et al., "Extend and Explain: Interpreting Very Long Language Models", Proceedings of Machine Learning Research, vol. 193, pp. 1-43, Nov. 28, 2022, arXiv:2209.01174v3.

* cited by examiner

400

Receive one or more document data objects
402

Generate one or more classifications based on the one or
more document data objects
404

Initiate the performance of one or more prediction-based
actions based on the one or more classifications
406

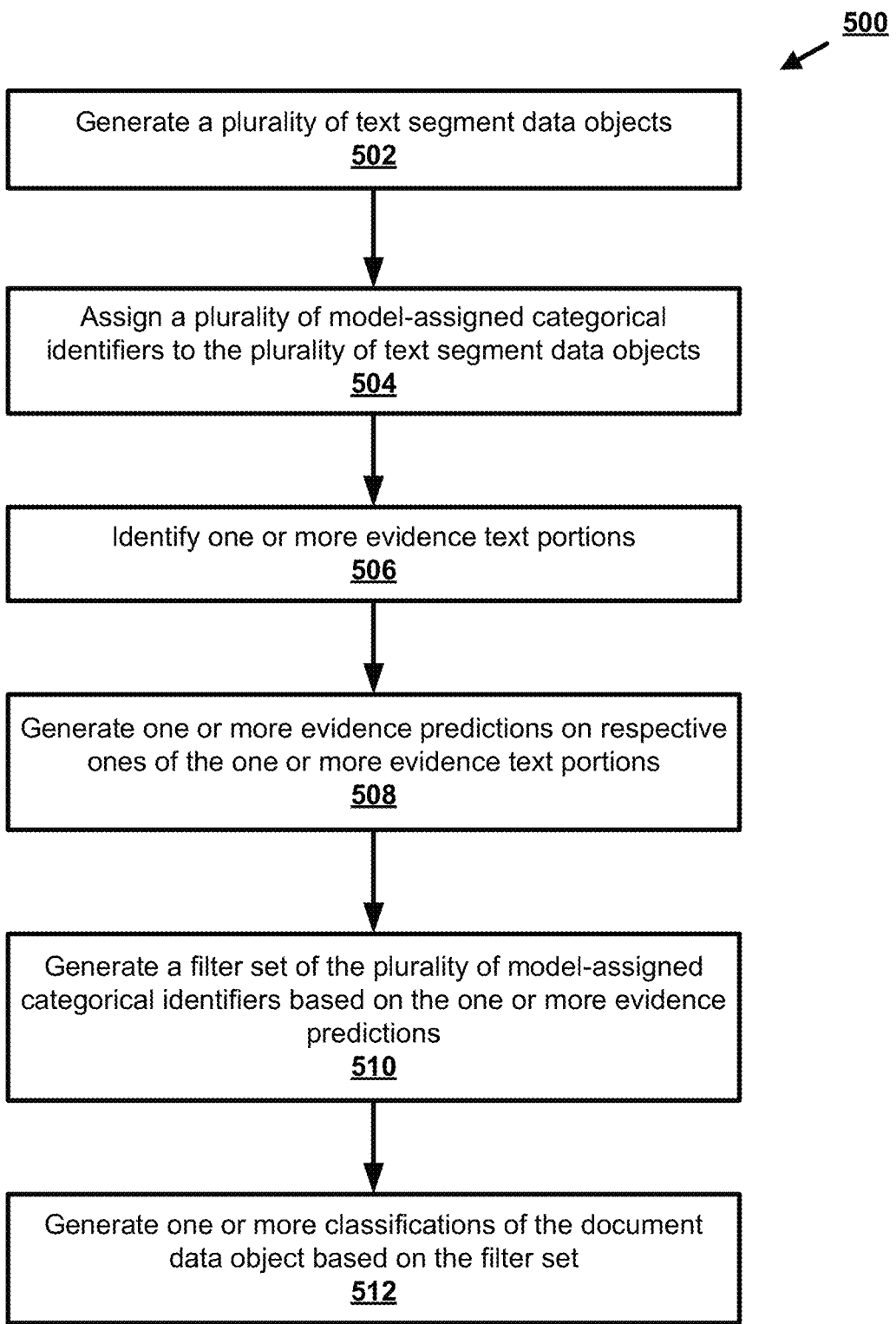

500

Generate a plurality of text segment data objects
502

Assign a plurality of model-assigned categorical identifiers to the plurality of text segment data objects
504

Identify one or more evidence text portions
506

Generate one or more evidence predictions on respective ones of the one or more evidence text portions
508

Generate a filter set of the plurality of model-assigned categorical identifiers based on the one or more evidence predictions
510

Generate one or more classifications of the document data object based on the filter set
512

Figure 6:
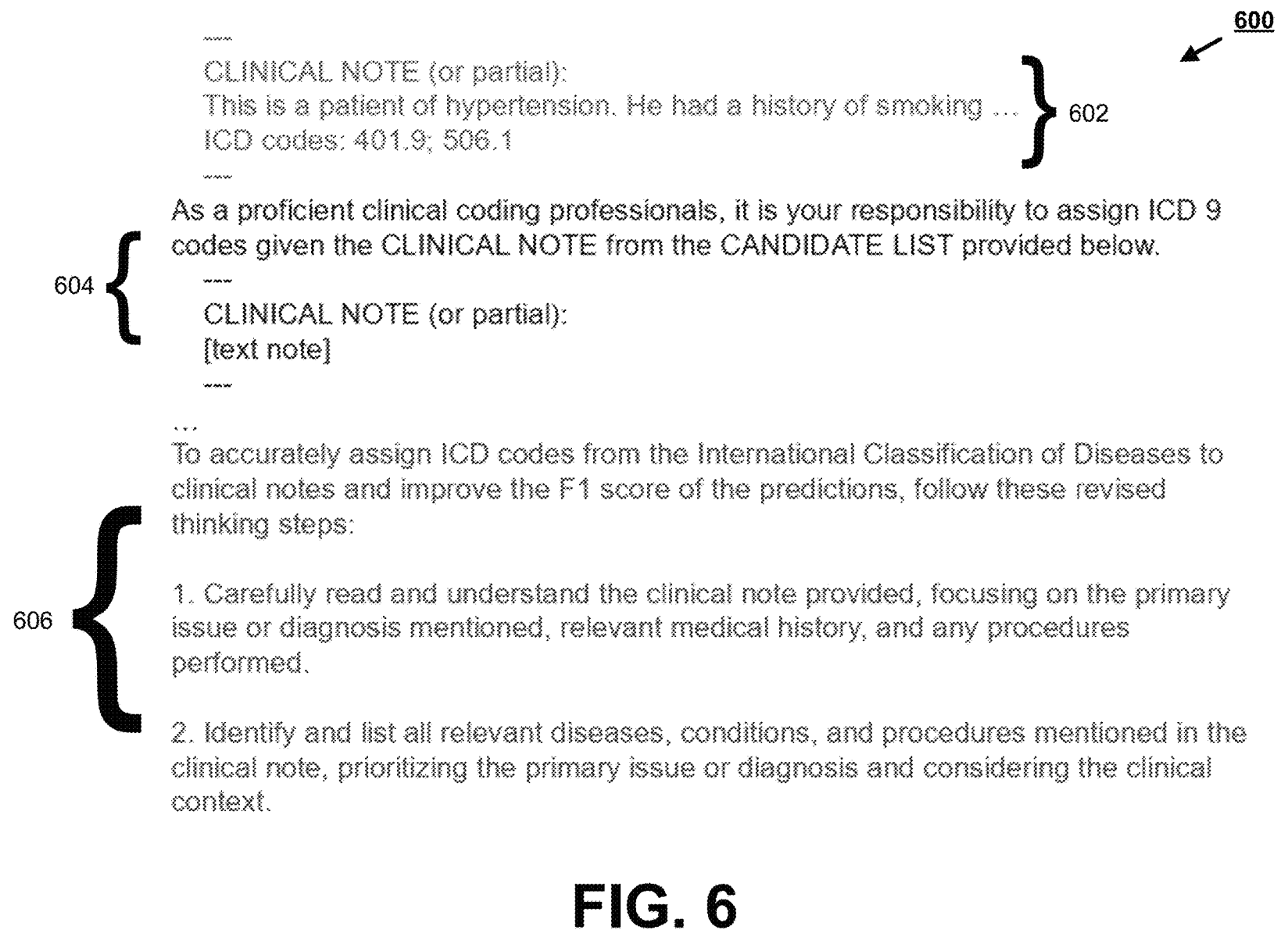

CLINICAL NOTE (or partial):
This is a patient of hypertension. He had a history of smoking ...
ICD codes: 401.9; 506.1

604

As a proficient clinical coding professionals, it is your responsibility to assign ICD 9 codes given the CLINICAL NOTE from the CANDIDATE LIST provided below.

CLINICAL NOTE (or partial):
[text note]

606

...:
To accurately assign ICD codes from the International Classification of Diseases to clinical notes and improve the F1 score of the predictions, follow these revised thinking steps:

1. Carefully read and understand the clinical note provided, focusing on the primary issue or diagnosis mentioned, relevant medical history, and any procedures performed.

2. Identify and list all relevant diseases, conditions, and procedures mentioned in the clinical note, prioritizing the primary issue or diagnosis and considering the clinical context.

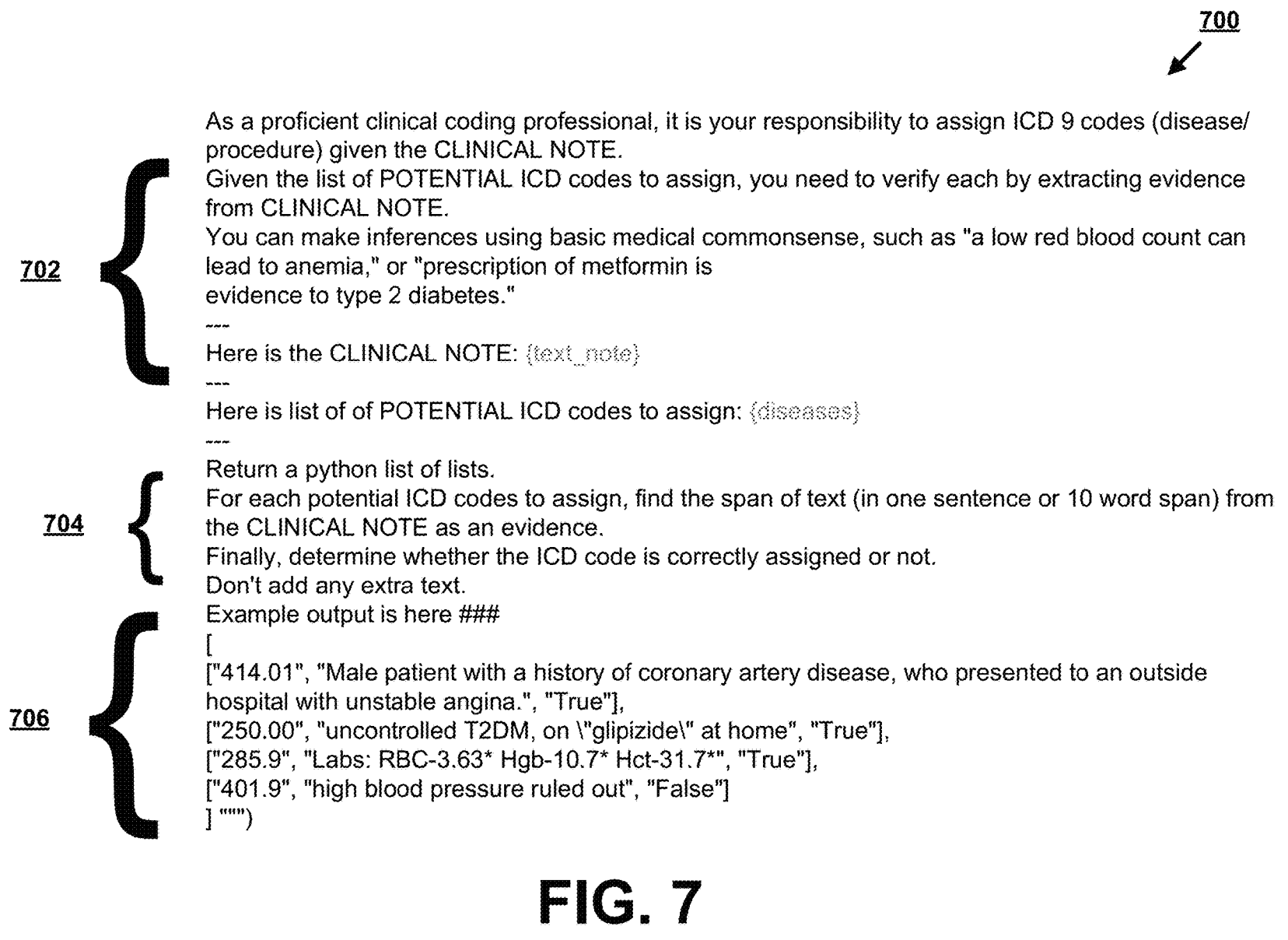

702
As a proficient clinical coding professional, it is your responsibility to assign ICD 9 codes (disease/procedure) given the CLINICAL NOTE.
Given the list of POTENTIAL ICD codes to assign, you need to verify each by extracting evidence from CLINICAL NOTE.
You can make inferences using basic medical commonsense, such as "a low red blood count can lead to anemia," or "prescription of metformin is evidence to type 2 diabetes."

---
Here is the CLINICAL NOTE: {{text_note}}
---
Here is list of of POTENTIAL ICD codes to assign: {{diseases}}
---

704
Return a python list of lists.
For each potential ICD codes to assign, find the span of text (in one sentence or 10 word span) from the CLINICAL NOTE as an evidence.
Finally, determine whether the ICD code is correctly assigned or not.
Don't add any extra text.

706
Example output is here ###
[
["414.01", "Male patient with a history of coronary artery disease, who presented to an outside hospital with unstable angina.", "True"],
["250.00", "uncontrolled T2DM, on \"glipizide\" at home", "True"],
["285.9", "Labs: RBC-3.63* Hgb-10.7* Hct-31.7*", "True"],
["401.9", "high blood pressure ruled out", "False"]
]"""")

FIG. 7

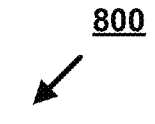

800

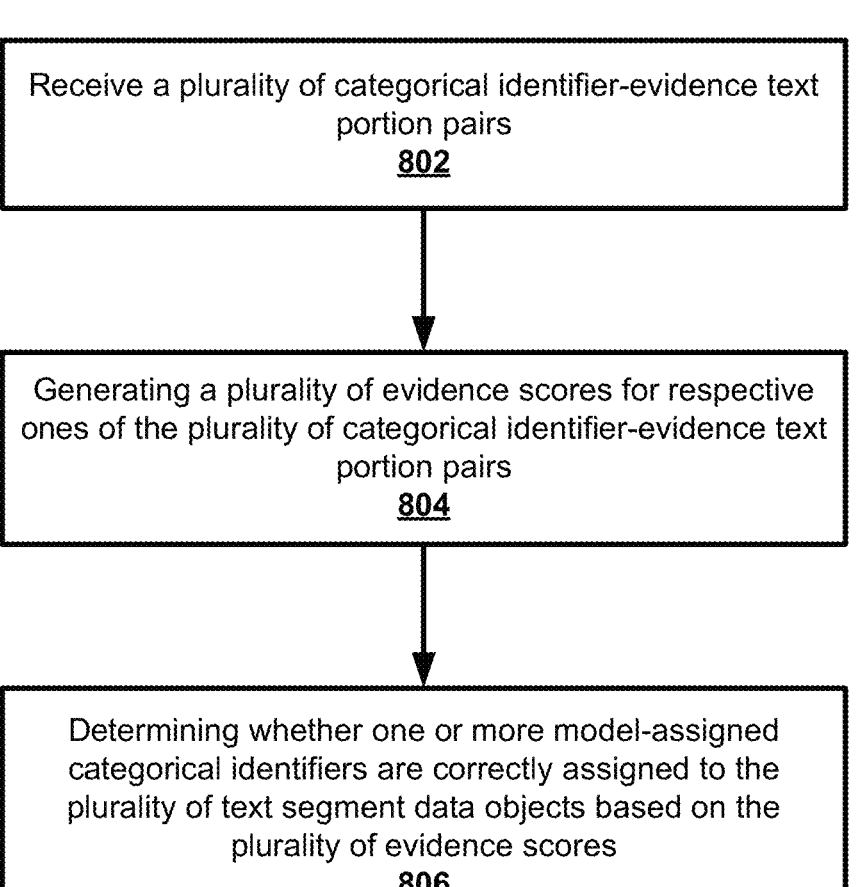

Receive a plurality of categorical identifier-evidence text portion pairs
802

Generating a plurality of evidence scores for respective ones of the plurality of categorical identifier-evidence text portion pairs
804

Determining whether one or more model-assigned categorical identifiers are correctly assigned to the plurality of text segment data objects based on the plurality of evidence scores
806

MACHINE LEARNING TECHNIQUES FOR CLASSIFYING DOCUMENT DATA OBJECTS

CROSS REFERENCE TO RELATED APPLICATION

This application claims the priority of U.S. Provisional Application No. 63/520,785, entitled "AUTOMATIC MEDICAL CODING FROM TEXT," filed on Aug. 21, 2023, the disclosure of which is hereby incorporated by reference in its entirety.

BACKGROUND

Various embodiments of the present disclosure address technical challenges related to performing document classification and provide solutions to address the efficiency and reliability shortcomings of existing document analysis solutions.

Tradition techniques for document classification, such as coding of medical documents, is labor intensive but may be automated to increase efficiencies while decreasing manual processing and associated costs. For example, risk adjustment coding may comprise identifying patients who have undocumented diseases by finding evidence of disease in the text of medical charts. In such an example, machine learning models may be used to analyze and generate classifications on text at scale to assist with identifying relevant medical charts from among tens of millions.

Traditionally, the performance of a machine learning model is evaluated based on the accuracy of its outputs, such as classifications. However, the explainability of how an output is generated may be leveraged to enhance model evaluations. That is, the ability to understand why, for a given data input (e.g., document), a machine learning model made a certain classification may be an important criterion for trusting the machine learning model's classifications. For example, medical coders, chart reviewers, and clinicians may benefit from medical document classification (coding) using a machine learning model that may provide sentence-level explainability. Additionally, explaining why a certain classification was made may be essential for a fair, auditable, and trustworthy machine learning model. Accordingly, being able to explain a machine learning model's decision process may be useful in correcting classifications derived from potentially biased information.

Traditionally, attribution maps may be created and used to explain machine learning model classifications. An attribution map may score features of an input by establishing an importance of each feature to obtain a specific classification outcome. However, attribution maps suffer from limited explanation robustness which lacks the transparency and credibility for reliably evaluating machine learning model classifications.

Various embodiments of the present disclosure make important contributions to traditional model evaluation techniques by addressing these technical challenges, among others.

BRIEF SUMMARY

In general, various embodiments of the present disclosure provide methods, apparatus, systems, computing devices, computing entities, and/or the like for classifying document data objects.

Various embodiments of the present disclosure make important technical contributions to improving classification accuracy of document classification systems by configuring a generative machine learning model to identify one or more evidence text portions comprising one or more bases relied on by the generative machine learning model for assigning a plurality of categorical identifiers to a plurality of text segment data objects associated with a document data object, and verifying the one or more evidence text portions with a verifier machine learning model to generate one or more classifications of the document data object and provide the one or more verified evidence text portions along with the one or more classifications.

As described herein, while generative machine learning models may be capable of differentiating domain-specific terms, traditional generative machine learning models are prone to generating predictions that are high in recall but low in precision (e.g., excessively predicting categorical identifiers). Some techniques of the present disclosure improve traditional generative machine learning models by leveraging a verifier machine learning model to refine predictions output by a model based on a verification of the evidence relied on to generate the predictions. By doing so, some of the techniques of the present disclosure improve model training and the adaptability of predictive machine learning models, trained based on historical data, to changing data trends.

In some embodiments, a computer-implemented method comprises: generating, by one or more processors, a plurality of text segment data objects associated with a document data object; assigning, by the one or more processors and using a first machine learning model, a plurality of model-assigned categorical identifiers to the plurality of text segment data objects; identifying, by the one or more processors and using the first machine learning model, one or more evidence text portions from the plurality of text segment data objects, the one or more evidence text portions comprising one or more bases relied on by the first machine learning model for the assigning; generating, by the one or more processors and using a second machine learning model, one or more evidence predictions on respective ones of the one or more evidence text portions; generating, by the one or more processors, a filter set of the plurality of model-assigned categorical identifiers based on the one or more evidence predictions; and generating, by the one or more processors, one or more classifications of the document data object based on the filter set.

In some embodiments, a computing system comprising memory and one or more processors communicatively coupled to the memory, the one or more processors configured to: generate a plurality of text segment data objects associated with a document data object; assign, using a first machine learning model, a plurality of model-assigned categorical identifiers to the plurality of text segment data objects; identify, using the first machine learning model, one or more evidence text portions from the plurality of text segment data objects, the one or more evidence text portions comprising one or more bases relied on by the first machine learning model for the assigning; generate, using a second machine learning model, one or more evidence predictions on respective ones of the one or more evidence text portions; generate a filter set of the plurality of model-assigned categorical identifiers based on the one or more evidence predictions; and generate one or more classifications of the document data object based on the filter set.

In some embodiments, one or more non-transitory computer-readable storage media including instructions that, when executed by one or more processors, cause the one or more processors to: generate a plurality of text segment data objects associated with a document data object; assign, using a first machine learning model, a plurality of model-assigned categorical identifiers to the plurality of text segment data objects; identify, using the first machine learning model, one or more evidence text portions from the plurality of text segment data objects, the one or more evidence text portions comprising one or more bases relied on by the first machine learning model for the assigning; generate, using a second machine learning model, one or more evidence predictions on respective ones of the one or more evidence text portions; generate a filter set of the plurality of model-assigned categorical identifiers based on the one or more evidence predictions; and generate one or more classifications of the document data object based on the filter set.

BRIEF DESCRIPTION OF THE DRAWINGS

FIG. 5 is a flowchart diagram of an example process for classifying document data objects in accordance with some embodiments of the present disclosure.

FIG. 6 depicts an operational example of a prompt command for assigning model-assigned categorical identifiers to text segment data objects in accordance with some embodiments of the present disclosure.

FIG. 7 depicts an operational example of a prompt command for identifying evidence text portions from text segment data objects in accordance with some embodiments of the present disclosure.

FIG. 8 is a flowchart diagram of an example process for generating evidence predictions in accordance with some embodiments of the present disclosure.

DETAILED DESCRIPTION

Figure 1:
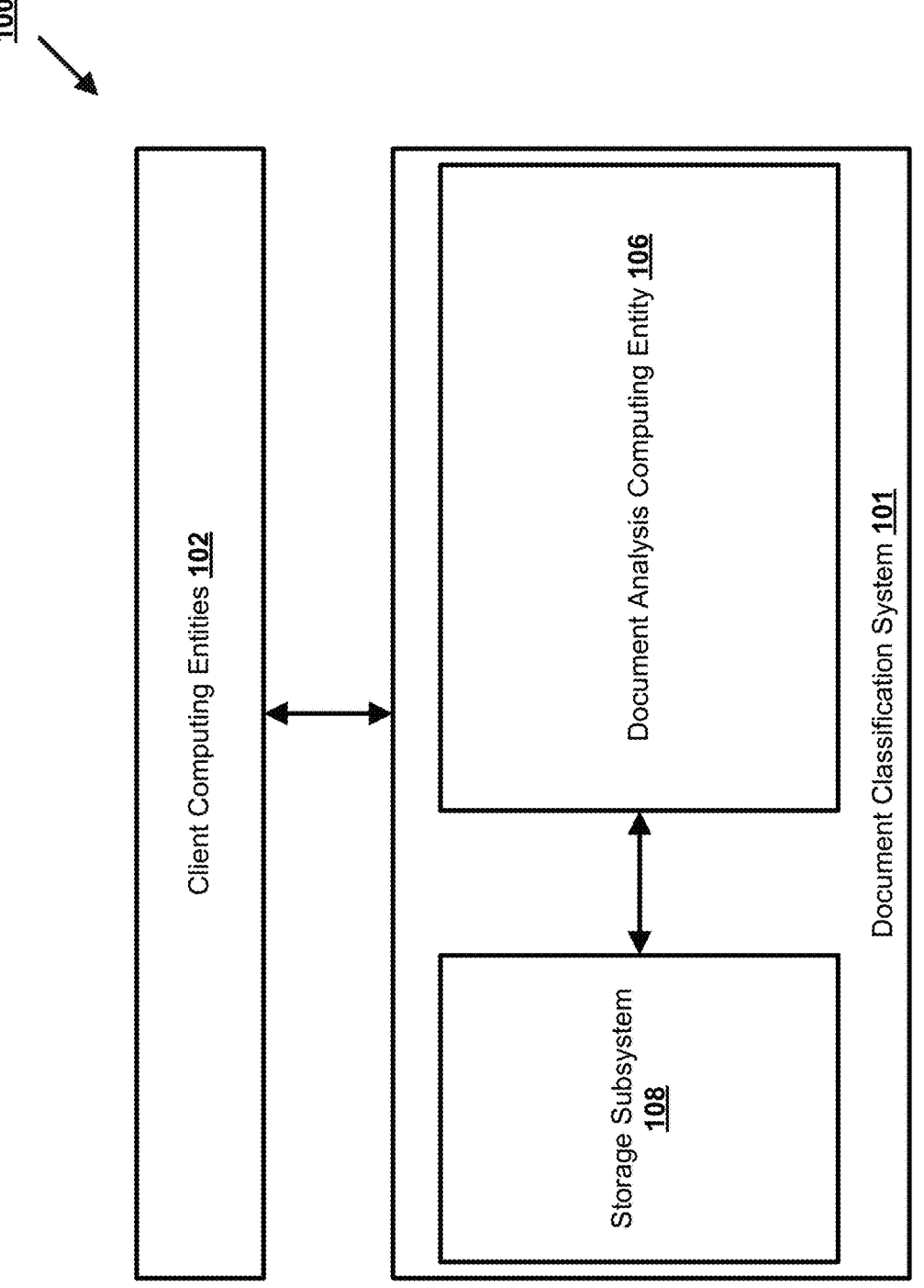
FIG. 1 provides an example overview of an architecture in accordance with some embodiments of the present disclosure.

Various embodiments of the present disclosure are described more fully hereinafter with reference to the accompanying drawings, in which some, but not all embodiments of the present disclosure are shown. Indeed, the present disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "example" are used to be examples with no indication of quality level. Terms such as "computing," "determining," "generating," and/or similar words are used herein interchangeably to refer to the creation, modification, or identification of data. Further, "based on," "based at least in part on," "based at least on," "based upon," and/or similar words are used herein interchangeably in an open-ended manner such that they do not necessarily indicate being based only on or based solely on the referenced element or elements unless so indicated. Like numbers refer to like elements throughout.

I. COMPUTER PROGRAM PRODUCTS, METHODS, AND COMPUTING ENTITIES

Embodiments of the present disclosure may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

A non-volatile computer-readable storage medium may include a floppy disk, flexible disk, hard disk, solid-state storage (SSS) (e.g., a solid-state drive (SSD), solid-state card (SSC), solid-state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

A volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatus, systems, computing devices, computing entities, and/or the like. As such, embodiments of the present disclosure may take the form of an apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises a combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some example embodiments, retrieval, loading, and/or execution may be performed in parallel such that multiple instructions are retrieved, loaded, and/or executed together. Thus, such embodiments may produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXAMPLE FRAMEWORK

FIG. 1 provides an example overview of an architecture 100 in accordance with some embodiments of the present disclosure. The architecture 100 includes a document classification system 101 configured to receive classification requests from client computing entities 102, process the classification requests to generate classifications, determine evidence text portions associated with the classifications, provide the generated classifications and the evidence text portions to the client computing entities 102, and automatically initiate performance of prediction-based actions based on the generated classifications. The example architecture 100 may be used in a plurality of domains and not limited to any specific application as disclosed herewith. The plurality of domains may include banking, healthcare, industrial, manufacturing, education, retail, to name a few.

An example of a prediction-based action that may be performed using the document classification system 101 comprises receiving a request for classifying a medical document, generating a classification of the medical document according to a taxonomy of classification identifiers, determining an evidence text portion associated with the classification, and displaying the classification and the evidence text portion on a user interface. Other examples of prediction-based actions comprise generating a diagnostic report, displaying/providing resources, generating, and/or executing action scripts, generating alerts or reminders, or generating one or more electronic communications based on the classification.

In accordance with various embodiments of the present disclosure, a document classification system may be configured to classify a document data object by assigning, using a generative machine learning model, categorical identifiers to a plurality of text segment data objects associated with the document data object, generating, using the generative machine learning model, a plurality of evidence text portions from the plurality of text segment data objects, and verifying, using a verifier machine learning model, the evidence text portions based on training with model-generated training labels and expert-labeled document data objects. As such, explainability, insight, and oversight of a decisioning process used by a document classification system to generate classifications document data objects may be provided. Accordingly, classifications generated based on predictions of a generative machine learning model may be refined based on verification, using a verifier machine learning model, of evidence the generative machine learning model relied on to make the predictions. This technique will lead to higher accuracy of performing document classifications. In doing so, the techniques described herein improve efficiency and speed of training predictive machine learning models, thus reducing the number of computational operations needed and/or the amount of training data entries needed to train predictive machine learning models. Accordingly, the techniques described herein improve the computational efficiency, storage-wise efficiency, and/or speed of training predictive machine learning models.

In some embodiments, document classification system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software, and/or firmware required to implement it (such as, e.g., network routers, and/or the like).

The document classification system 101 may include a document analysis computing entity 106 and a storage subsystem 108. The document analysis computing entity 106 may be configured to receive classification requests from one or more client computing entities 102, process the classification requests to generate classifications corresponding to the classification requests, determine evidence text portions associated with the classifications, provide the generated classifications and the evidence text portions to the client computing entities 102, and automatically initiate performance of prediction-based actions based on the generated classifications.

The storage subsystem 108 may be configured to store input data used by the document analysis computing entity 106 to perform document analysis as well as model definition data used by the document analysis computing entity 106 to perform various classification and/or predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

A. Example Document Analysis Computing Entity

Figure 2:
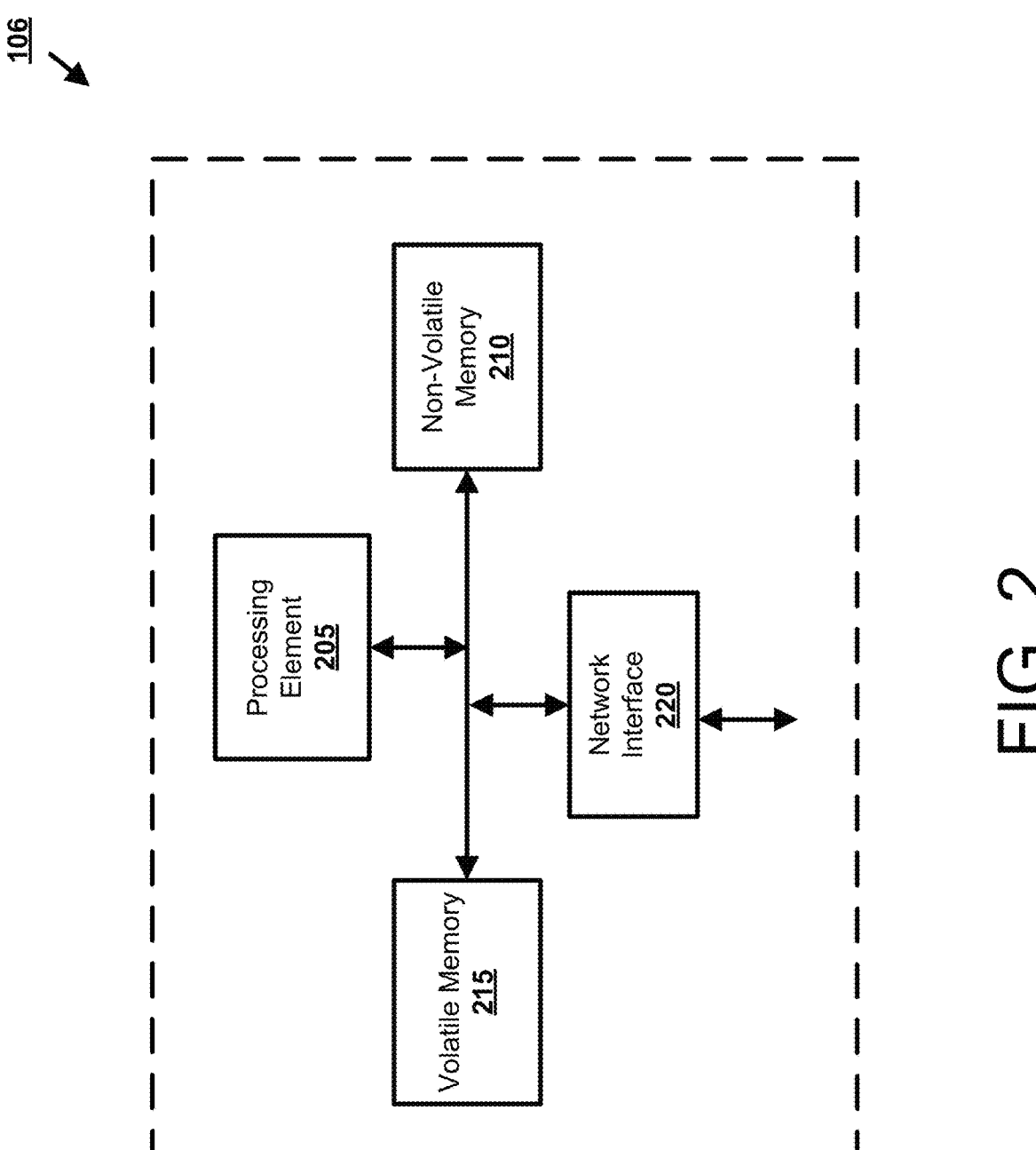
FIG. 2 provides an example document analysis computing entity in accordance with some embodiments of the present disclosure.

FIG. 2 provides an example document analysis computing entity 106 in accordance with some embodiments of the present disclosure. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In some embodiments, these functions, operations, and/or processes may be performed on data, content, information, and/or similar terms used herein interchangeably.

As shown in FIG. 2, in some embodiments, the document analysis computing entity 106 may include, or be in communication with, one or more processing elements 205 (also referred to as processors, processing circuitry, and/or similar terms used herein interchangeably) that communicate with other elements within the document analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In some embodiments, the document analysis computing entity 106 may further include, or be in communication with, non-volatile media (also referred to as non-volatile storage, memory, memory storage, memory circuitry, and/or similar terms used herein interchangeably). In some embodiments, the non-volatile storage or memory may include one or more non-volatile memory 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In some embodiments, the document analysis computing entity 106 may further include, or be in communication with, volatile media (also referred to as volatile storage, memory, memory storage, memory circuitry, and/or similar terms used herein interchangeably). In some embodiments, the volatile storage or memory may also include one or more volatile memory 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the document analysis computing entity 106 with the assistance of the processing element 205 and operating system.

As indicated, in some embodiments, the document analysis computing entity 106 may also include one or more network interfaces 220 for communicating with various computing entities, such as by communicating data, content, information, and/or similar terms used herein interchangeably that may be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the document analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the document analysis computing entity 106 may include, or be in communication with, one or more input elements, such as a keyboard input, a mouse input, a touch screen/display input, motion input, movement input, audio input, pointing device input, joystick input, keypad input, and/or the like. The document analysis computing entity 106 may also include, or be in communication with, one or more output elements (not shown), such as audio output, video output, screen/display output, motion output, movement output, and/or the like.

B. Example Client Computing Entity

Figure 3:
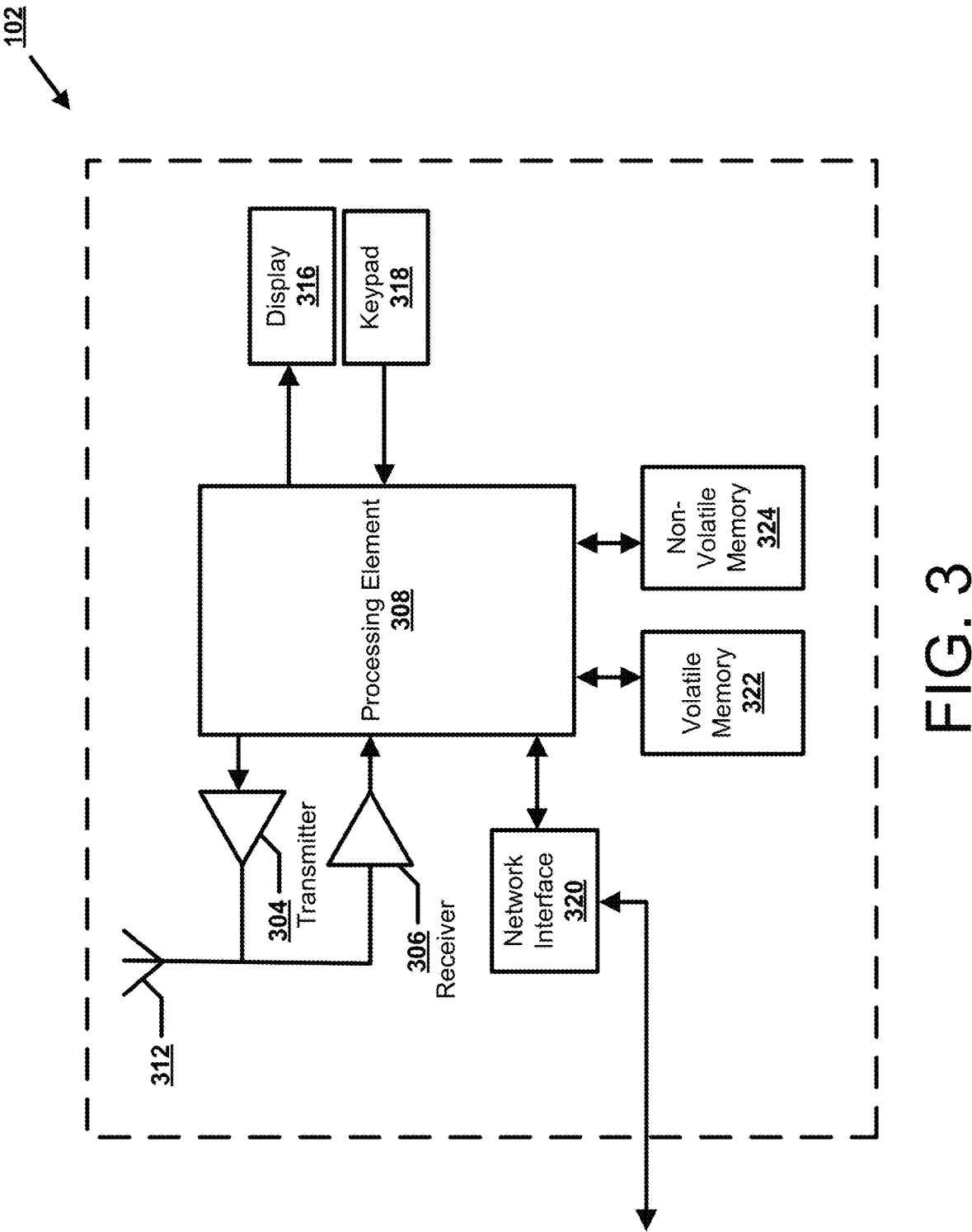
FIG. 3 provides an example client computing entity in accordance with some embodiments of the present disclosure.

FIG. 3 provides an example client computing entity in accordance with some embodiments of the present disclosure. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 may be operated by various parties. As shown in FIG. 3, the client computing entity 102 may include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the document analysis computing entity 106. In some embodiments, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the document analysis computing entity 106 via a network interface 320.

Via these communication standards and protocols, the client computing entity 102 may communicate with various other entities using mechanisms such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 may also download changes, add-ons, and updates, for instance, to its firmware, software (e.g., including executable instructions, applications, program modules), and operating system.

According to some embodiments, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In some embodiments, the location module may acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data may be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data may be determined by triangulating the position of the client computing entity 102 in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops), and/or the like. For instance, such technologies may include the iBeacons, Gimbal proximity beacons, Bluetooth Low Energy (BLE) transmitters, NFC transmitters, and/or the like. These indoor positioning aspects may be used in a variety of settings to determine the location of someone or something to within inches or centimeters.

The client computing entity 102 may also comprise a user interface (that may include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the document analysis computing entity 106, as described herein. The user input interface may comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 may include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface may be used, for example, to activate or deactivate certain functions, such as screen savers and/or sleep modes.

The client computing entity 102 may also include volatile memory 322 and/or non-volatile memory 324, which may be embedded and/or may be removable. For example, the non-volatile memory 324 may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory 322 may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile memory may store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the client computing entity 102 or accessible through a browser or other user interface for communicating with the document analysis computing entity 106 and/or various other computing entities.

In another embodiment, the client computing entity 102 may include one or more components or functionalities that are the same or similar to those of the document analysis computing entity 106, as described in greater detail above. As will be recognized, these architectures and descriptions are provided for example purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

III. EXAMPLES OF CERTAIN TERMS

In some embodiments, the term "text segment data object" refers to a data construct that describes one of a plurality of parts comprising a document data object. For example, a plurality of text segment data objects may be generated by segmenting a document data object into a predetermined number of parts. In some embodiments, a text segment data object may comprise text data associated with one or more sentences or paragraphs. In some embodiments, a document data object may be divided into a plurality of text segment data objects such that the document data object may be processed or analyzed as individual text segment data objects.

In some embodiments, the term "document data object" refers to a data construct that describes a body of text. In one example embodiment, a document data object comprises text data associated with medical documents, such as patient charts and discharge summaries. A document data object may comprise text associated with one or more topics or features of which the document data object may be classified based on one or more categorical identifiers. According to various embodiments of the present disclosure, a plurality of text segment data objects may be generated from a document data object.

In some embodiments, the term "categorical identifier" refers to a data construct that describes a sequence of characters, numbers, symbols, or any combination thereof associated with a categorical description. According to various embodiments of the present disclosure, a model-assigned categorical identifier may be assigned to a text segment data object as a step towards generating a classification for a document data object. One or more categorical identifiers may be assigned to one or more text segment data objects based on an association of one or more evidence text portions from a document data object (or text segment data objects associated with the document data object) with a plurality of categorical descriptions associated with a plurality of candidate categorical identifiers. In one example embodiment, categorical identifiers may comprise diagnostic codes (e.g., International Classification of Diseases (ICD)

or Current Procedural Terminology (CPT) codes) associated with diagnoses or treatments healthcare providers may perform.

In some embodiments, the term "evidence text portion" refers to a data construct that describes a part of a text segment data object comprising a basis relied on by a generative machine learning model for assigning one or more categorical identifiers to the text segment data object or a document data object comprising the text segment data object. Evidence text portions may be identified from a text segment data object based on an attribution of the evidence text portions to a selection of one or more model-assigned categorical identifiers (from a plurality of candidate categorical identifiers) for assignment to the text segment data object or document data object. In some embodiments, identifying evidence text portions comprises either generating or receiving one or more prompt commands and providing the one or more prompt commands to a generative machine learning model. The one or more prompt commands may instruct the generative machine learning model to extract text from one or more text segment data objects that contribute to assignment of one or more categorical identifiers to the one or more text segment data objects. In some embodiments, one or more prompt commands comprising one or more examples, one or more analysis inputs, and an instruction to follow (e.g., identifying evidence text portions) and repeat based on the one or more examples and the one or more analysis inputs are provided to a machine learning model. Based on the one or more prompt commands, the generative machine learning model may generate an output, e.g., identify one or more evidence text portions.

In some embodiments, the term "model-assigned categorical identifier" refers to a data construct that describes a categorical identifier that is assigned to one or more text segments or a document data object by a generative machine learning model. According to various embodiments of the present disclosure, assigning model-assigned categorical identifiers to a plurality of text segment data objects comprises (i) receiving a plurality of candidate categorical identifiers and a respective plurality of categorical descriptions, (ii) selecting, for the plurality of text segment data objects, one or more model-assigned categorical identifiers from the plurality of candidate categorical identifiers, and (iii) generating one or more categorical predictions based on the selected one or more model-assigned categorical identifiers. In some embodiments, assigning a model-assigned categorical identifier comprises either generating or receiving one or more prompt commands and providing the one or more prompt commands to a generative machine learning model. The one or more prompt commands may instruct the generative machine learning model to assign categorical identifiers (model-assigned categorical identifiers) to one or more text segment data objects of a document data object.

In some embodiments, the term "prompt command" refers to a data construct that describes instructions for initiating in-context learning (ICL) with a generative machine learning model. ICL may comprise a generative machine learning model learning to generate relevant and accurate responses based on a prompt command. A prompt command may comprise a context to analyze comprising one or more examples, one or more analysis inputs, and a task-specific instruction to follow and repeat based on the one or more examples and the one or more analysis inputs (e.g., assigning model-assigned categorical identifiers or identifying evidence text portions). Via a command prompt, a generative machine learning model may adapt its knowledge after each instruction execution and generate a suitable output.

In some embodiments, the term "categorical description" refers to a data construct that describes one or more keywords, numbers, or phrases associated with a classification according to a given taxonomy. A document data object or one or more text segment data objects of the document data object may comprise features that may be described by one or more categorical descriptions. In some embodiments, one or more categorical identifiers associated with the one or more categorical descriptions are assigned to a document data object or one or more text segment data objects associated with the document data object. In one example embodiment, a categorical description may comprise a description of diagnostic codes (e.g., International Classification of Diseases (ICD) or Current Procedural Terminology (CPT) codes) associated with diagnoses or treatments healthcare providers may perform.

In some embodiments, the term "categorical identifier-evidence text portion pair" refers to a data construct that describes a grouping of a categorical identifier with an evidence text portion. According to various embodiments of the present disclosure, a generative machine learning model is configured to identify one or more evidence text portions from one or more text segment data objects associated with respective one or more categorical identifiers. Each of the identified one or more evidence text portions may thereby form a categorical identifier-evidence text portion pair with the respective one or more categorical identifiers. In some embodiments, one or more categorical identifier-evidence text portion pairs may be used in combination with one or more model-generated training labels and one or more expert-labeled document data objects to generate one or more weights of a verifier machine learning model configured to generate one or more evidence predictions on one or more evidence text portions.

In some embodiments, the term "model-generated training label" refers to a data construct that describes training data comprising a classification that is generated by a generative machine learning model. For example, a model-generated training label may comprise a model-assigned categorical identifier that is tagged or identified with a text segment data object by the generative machine learning model.

In some embodiments, the term "expert-labeled document data object" refers to a data construct that describes a document data object, one or more text segment data objects, or generally text data objects that is/are labeled with one or more categorical identifiers by an expert user.

In some embodiments, the term "evidence score" refers to a data construct that describes a measurement or value representative of how well an evidence text portion is able to characterize or support an assignment of a particular categorical identifier, e.g., to a text segment data object or a document data object. For example, an evidence score may be representative of a degree of attribution of an evidence text portion to a classification (e.g., of a document data object). As such, evidence scores may be used to identify evidence text portions that are most relevant to a classification of a document data object with respect to a particular model-assigned categorical identifier. According to various embodiments of the present disclosure, an evidence score may be generated for each of one or more evidence text portions associated with a categorical identifier-evidence text portion pair by a verifier machine learning model based on evidence predictions on respective ones of the one or more evidence text portions. In some embodiments, an evidence score may be generated by row max pooling one or more evidence predictions associated with one or more categorical identifier-evidence text portion pairs comprising a given categorical identifier. In some embodiments, evidence text portions comprising highest evidence scores may be identified and provided along with one or more classifications of a document data object, e.g., for the purposes of explainability or providing reasoning for the one or more classifications.

In some embodiments, the term "filter set" refers to a data construct that describes a set of model-assigned categorical identifiers selected from a plurality of model-assigned categorical identifiers based on one or more evidence predictions generated by a verifier machine learning model. A filter set may be generated to refine (e.g., improve precision) a plurality of model-assigned categorical identifiers (e.g., high recall) that are assigned to text segment data objects of a document data object by a generative machine learning model. According to various embodiments of the present disclosure, one or more classifications of a document data object is generated based on a filter set of model-assigned categorical identifiers.

In some embodiments, the term "classification" refers to a data construct that describes an identification of one or more features associated with a document data object. For example, a classification of a document data object may comprise an association of a document data object with a categorical identifier. According to various embodiments of the present disclosure, a classification of a document data object is generated by (i) generating a plurality of text segment data objects associated with a document data object, (ii) assigning, using a generative machine learning model, a plurality of model-assigned categorical identifiers to the plurality of text segment data objects, (iii) identifying, using the generative machine learning model, one or more evidence text portions from the plurality of text segment data objects, the one or more evidence text portions comprising ones or more bases relied on by the first machine learning model for the assigning, (iv) generating, using a verifier machine learning model, one or more evidence predictions on respective ones of the one or more evidence text portions, (v) generating a filter set of the plurality of model-assigned categorical identifiers based on the one or more evidence predictions, and (vi) generating one or more classifications of the document data object based on the filter set.

In some embodiments, the term "evidence prediction" refers to a data construct that describes an output generated by a verifier machine learning model representative of an accuracy or predictive quality of an evidence text portion with respect to a classification of a document data object. Evidence predictions may be generated for evidence text portions associated with a plurality of model-assigned categorical identifiers and used to refine or filter the plurality of model-assigned categorical identifiers. For example, evidence predictions may confirm or verify the model-assigned categorical identifiers. In some embodiments, a verifier machine learning model may be trained to generate evidence predictions on evidence text portions to evaluate bases for assigning certain categorical identifiers to text segment data objects or a document data object by a generative machine learning model. According to various embodiments of the present disclosure, (i) a verifier machine learning model is configured and/or used to generate one or more evidence predictions on respective ones of one or more evidence text portions associated with a plurality of model-assigned categorical identifiers, wherein the plurality of model-assigned categorical identifiers are assigned to a plurality of text segment data objects associated with a document data object, (ii) a filter set of the plurality of model-assigned categorical identifiers is generated based on the one or more evidence predictions, and (iii) one or more classifications are generated for the document data object based on the filter set. In some embodiments, a verifier machine learning model is configured and/or used to generate one or more evidence predictions on one or more evidence text portions based on one or more weights trained on ground truth data comprising one or more model-generated training labels and/or one or more expert-labeled document data objects.

In some embodiments, the term "generative machine learning model" refers to a data construct that describes parameters, hyperparameters, and/or defined operations of a machine learning model that is configured to assign a plurality of model-assigned categorical identifiers to a plurality of text segment data objects and identify one or more evidence text portions from the plurality of text segment data objects. In some embodiments, a generative machine learning model is configured to perform a multi-label binary classification comprising selecting one or more categorical identifiers from a plurality of candidate categorical identifiers and assigning the one or more categorical identifiers to one or more text segment data objects associated with a document data object. In some embodiments, a generative machine learning model comprises a large language model (LLM). The LLM may be any general LLM or any pre-trained and fine-tuned generative model, such as a generative pre-trained transformer. For example, a generative machine learning model may be pre-trained on a relatively broad-scoped dataset (e.g., than that of a fine-tuning dataset) usable by the generative machine learning model to learn general functionalities that may help the generative machine learning model perform a specific task upon fine-tuning. In some embodiments, a generative machine learning model may be fine-tuned on medical text data, such as electronic health record (EHR) or claims data from electronic medical records (EMR) or databases.

In some embodiments, the term "verifier machine learning model" refers to a data construct that describes parameters, hyperparameters, and/or defined operations of a machine learning model that is configured to generate evidence predictions on evidence text portions. A verifier machine learning model may be trained to generate evidence predictions on evidence text portions to evaluate bases for assigning certain categorical identifiers to text segment data objects or a document data object by a generative machine learning model. In some embodiments, a verifier machine learning model is configured to generate evidence predictions by (i) receiving a plurality of categorical identifier-evidence text portion pairs comprising (a) a plurality of evidence text portions determined from a plurality of text segment data objects by a generative machine learning model as supporting a respective plurality of classifications associated with a plurality of candidate categorical identifiers and (b) the plurality of candidate categorical identifiers, (ii) generating a plurality of evidence scores for respective ones of the plurality of categorical identifier-evidence text portion pairs, and (iii) determining whether one or more model-assigned categorical identifiers, assigned to the plurality of text segment data objects by the generative machine learning model, are correctly assigned to the plurality of text segment data objects based on the plurality of evidence scores. In some embodiments, a verifier machine learning model is configured and/or used to generate one or more evidence predictions on one or more evidence text portions based on one or more weights trained on ground truth data comprising one or more model-generated training labels and/or one or more expert-labeled document data objects. In some embodiments, training one or more weights of a verifier machine learning model comprises determining one or more loss values based on a difference between one or more evidence predictions generated by the verifier machine learning and one or more model-generated training labels or one or more expert-labeled document data objects. In some embodiments, one or more categorical identifier-evidence text portion pairs may be used in combination with one or more model-generated training labels and one or more expert-labeled document data objects to generate one or more weights of a verifier machine learning model configured to generate one or more evidence predictions on one or more evidence text portions.

In some embodiments, the term "loss value" refers to a data construct that describes a numerical value representative of how well a machine learning model is able to correctly generate a given prediction. For example, low loss values may be representative of accurate predictions, while conversely, higher loss values may be representative of incorrect predictions. As such, a machine learning model may be trained to minimize loss values for predictions generated by the machine learning model. A loss value may be determined based on supervision or validation of one or more confidence scores associated with one or more predictions with ground truth data comprising one or more model-generated training labels and/or one or more expert-labeled document data objects. In some embodiments, training a verifier machine learning model comprises (i) generating a plurality of prediction loss values by (a) normalizing the plurality of evidence predictions and (b) determining a cross-entropy of the normalized plurality of evidence predictions, (ii) generating a plurality of confidence scores by row max pooling the plurality of evidence predictions, (iii) generating a plurality of weights by normalizing the plurality of confidence scores, (iv) generating a categorical identifier loss value comprising a sum based on the plurality of prediction loss values and the plurality of weights, (v) supervising or validating the plurality of confidence scores with ground truth data comprising one or more model-generated training labels and/or one or more expert-labeled document data objects, (vi) generating an evidence loss value by (a) normalizing the supervised/validated plurality of confidence scores based on a sigmoid function and (b) determining a binary cross-entropy of the normalized and supervised/validated plurality of confidence scores, and (vii) generating a total loss value based on the categorical identifier loss value and the evidence loss value.

IV. OVERVIEW

Various embodiments of the present disclosure make important technical contributions to improving classification accuracy of document classification systems by configuring a generative machine learning model to identify one or more evidence text portions comprising one or more bases relied on by the generative machine learning model for assigning a plurality of categorical identifiers to a plurality of text segment data objects associated with a document data object, and verifying the one or more evidence text portions with a verifier machine learning model to generate one or more classifications of the document data object and provide the one or more verified evidence text portions along with the one or more classifications. This approach improves training speed and training efficiency of training predictive machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative machine learning model architectures. Accordingly, techniques that improve predictive accuracy without harming training speed, such as the techniques described herein, enable improving training speed given a constant predictive accuracy. In doing so, the techniques described herein improve efficiency and speed of training predictive machine learning models, thus reducing the number of computational operations needed and/or the amount of training data entries needed to train predictive machine learning models. Accordingly, the techniques described herein improve the computational efficiency, storage-wise efficiency, and/or speed of training machine learning models.

For example, various embodiments of the present disclosure improve predictive accuracy of predictive machine learning models by configuring a generative machine learning model to identify one or more evidence text portions comprising one or more bases relied on by the generative machine learning model for assigning a plurality of categorical identifiers to a plurality of text segment data objects associated with a document data object, and verifying the one or more evidence text portions with a verifier machine learning model to generate one or more classifications of the document data object and provide the one or more verified evidence text portions along with the one or more classifications. As described herein, rule-based systems may be used to extract information from documents and assign categorical identifiers to the documents based on the extracted information. However, certain domain-specific terms (e.g., jargons, slangs, or lingos), such as those used in the medical field, are challenging for rule-based systems. For example, long medical documents, such as patient charts and discharge summaries, may comprise an abundance of clinically related terms.

LLMs, such as generative pre-trained transformers may be capable of differentiating domain-specific terms by training on the domain-specific terms. However, providing an entire medical document as context to LLM does not lead to the best performance on information extraction tasks. That is, while generative machine learning models may be capable of differentiating domain-specific terms, generative machine learning models tend to generate predictions that are high in recall but low in precision (e.g., excessively predicting categorical identifiers that may or may not be correct). Hence, a prediction validator may be needed to verify prediction outputs generated by generative machine learning models.

However, in accordance with various embodiments of the present disclosure, a document classification system may be configured to classify a document data object by assigning, using a generative machine learning model, categorical identifiers to a plurality of text segment data objects associated with the document data object, generating, using the generative machine learning model, a plurality of evidence text portions from the plurality of text segment data objects, and verifying, using a verifier machine learning model, the evidence text portions based on training with model-generated training labels and expert-labeled document data objects. As such, explainability, insight, and oversight of a decisioning process used by a document classification system to generate classifications document data objects may be provided via the evidence text portions. Accordingly, classifications generated based on predictions of a generative machine learning model may be refined based on verification, using a verifier machine learning model, of evidence the generative machine learning model relied on to make the predictions. In this manner, some of the techniques of the present disclosure, improve accuracy of performing document classifications. In doing so, the techniques described herein improve efficiency and speed of training predictive machine learning models, thus reducing the number of computational operations needed and/or the amount of training data entries needed to train predictive machine learning models. Accordingly, the techniques described herein improve the computational efficiency, storage-wise efficiency, and/or speed of training predictive machine learning models. Other technical improvements and advantages may be realized by one of ordinary skill in the art.

V. EXAMPLE SYSTEM OPERATIONS

As indicated, various embodiments of the present disclosure make important technical contributions to improving classification accuracy of document classification systems by configuring a generative machine learning model to identify one or more evidence text portions comprising one or more bases relied on by the generative machine learning model for assigning a plurality of categorical identifiers to a plurality of text segment data objects associated with a document data object, and verifying the one or more evidence text portions with a verifier machine learning model to generate one or more classifications of the document data object and provide the one or more verified evidence text portions along with the classifications. This approach improves training speed and training efficiency of training predictive machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative machine learning model architectures. Accordingly, techniques that improve predictive accuracy without harming training speed, such as the techniques described herein, enable improving training speed given a constant predictive accuracy. In doing so, the techniques described herein improve efficiency and speed of training predictive machine learning models, thus reducing the number of computational operations needed and/or the amount of training data entries needed to train predictive machine learning models. Accordingly, the techniques described herein improve the computational efficiency, storage-wise efficiency, and/or speed of training machine learning models.

Figure 4:
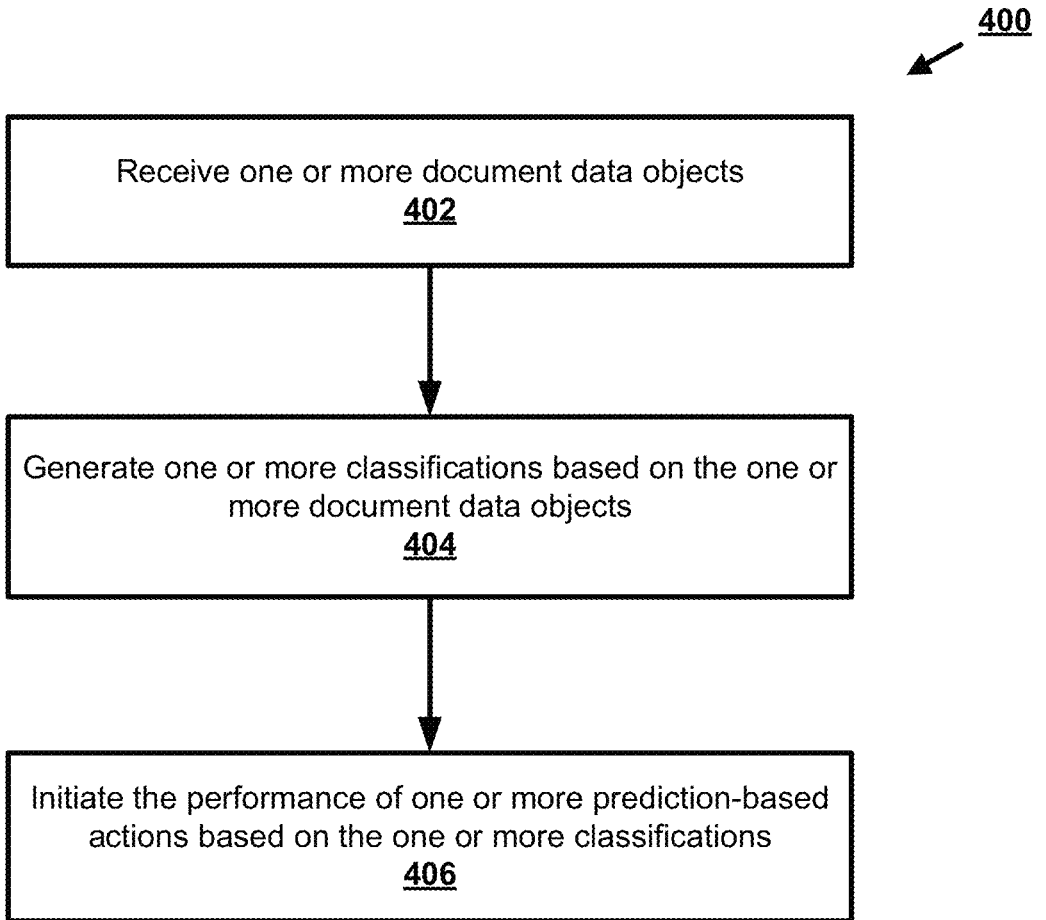
FIG. 4 is a flowchart diagram of an example process for performing predictive actions in accordance with some embodiments of the present disclosure.

FIG. 4 is a flowchart diagram of an example process for performing predictive actions in accordance with some embodiments of the present disclosure.

In some embodiments, the process 400 begins at step/operation 402 when the document analysis computing entity 106 receives one or more document data objects. In some embodiments, a document data object describes a body of text. In one example embodiment, a document data object comprises text data associated with medical documents, such as patient charts and discharge summaries. A document data object may comprise text associated with one or more topics or features of which the document data object may be classified based on one or more categorical identifiers.

In some embodiments, at step/operation 404, the document analysis computing entity 106 generates one or more classifications based on the one or more document data objects. In some embodiments, a classification describes an identification of one or more features associated with a document data object. For example, a classification of a document data object may comprise an association of a document data object with a categorical identifier. In some embodiments, generating the one or more classifications further comprises providing one or more evidence text portions associated with the one or more classifications. Classifying document data objects is described in further is described in further detail with respect to the description of FIG. 5.

In some embodiments, at step/operation 406, the document analysis computing entity 106 initiates the performance of one or more prediction-based actions based on the one or more classifications. In some embodiments, initiating the performance of the one or more prediction-based actions based on the one or more classifications includes displaying the one or more classifications of the one or more document data objects (and optionally, the one or more evidence text portions associated with the one or more classifications) using a prediction output user interface. For example, a prediction output user interface may display a list of top classifications for each of the one or more document data objects along with evidence text portions supporting the classifications. Initiating the performance of the one or more prediction-based actions based on the one or more classifications further comprises, for example, performing a resource-based action (e.g., allocation of resource), generating a diagnostic report, generating and/or executing action scripts, generating alerts or messages, or generating one or more electronic communications. The one or more prediction-based actions may further include displaying visual renderings of the aforementioned examples of prediction-based actions in addition to values, charts, and representations associated with the one or more classifications using a prediction output user interface.

FIG. 5 is a flowchart diagram of an example process for classifying document data objects in accordance with some embodiments of the present disclosure.

In some embodiments, the process 500 begins at step/operation 502 when the document analysis computing entity 106 generates a plurality of text segment data objects associated with a document data object. The plurality of text segment data objects may be generated by segmenting the document data object. In some embodiments, a text segment data object describes one of a plurality of parts comprising a document data object. In some embodiments, a text segment data object may comprise text data associated with one or more sentences or paragraphs. For example, the plurality of text segment data objects may be generated by segmenting the document data object into a predetermined number of parts.

In some embodiments, a document data object may be long or large in size (e.g., large volume of text) and may be segmented into multiples pieces (text segment data objects). According to various embodiments of the present disclosure, the document data object may be divided into a plurality of text segment data objects such that the document data object may be processed or analyzed as individual text segment data objects. In some embodiments, the amount and/or size of text segment data objects of which a document data object is divided is configurable. In some embodiments, a document data object is divided into a plurality of text segment data objects comprising chunks of equal size, or chunks of one or more sentence segments or paragraphs.

In some embodiments, at step/operation 504, the document analysis computing entity 106 assigns, using a generative machine learning model, a plurality of model-assigned categorical identifiers to the plurality of text segment data objects.

In some embodiments, a categorical identifier describes a sequence of characters, numbers, symbols, or any combination thereof associated with a categorical description. According to various embodiments of the present disclosure, one or more model-assigned categorical identifiers may be assigned to a text segment data object as a step towards generating a classification for a document data object. One or more categorical identifiers may be assigned to one or more text segment data objects based on an association of one or more evidence text portions from a document data object (or text segment data objects associated with the document data object) with a plurality of categorical descriptions associated with a plurality of candidate categorical identifiers. In one example embodiment, categorical identifiers may comprise diagnostic codes (e.g., International Classification of Diseases (ICD) or Current Procedural Terminology (CPT) codes) associated with diagnoses or treatments healthcare providers may perform.

In some embodiments, a categorical description describes one or more keywords, numbers, or phrases associated with a classification according to a given taxonomy. A document data object or one or more text segment data objects of the document data object may comprise features that may be described by one or more categorical descriptions. In one example embodiment, a categorical description may comprise a description of diagnostic codes (e.g., International Classification of Diseases (ICD) or Current Procedural Terminology (CPT) codes) associated with diagnoses or treatments healthcare providers may perform.

In some embodiments, a model-assigned categorical identifier describes a categorical identifier that is assigned to one or more text segments or a document data object by a generative machine learning model. According to various embodiments of the present disclosure, assigning model-assigned categorical identifiers to a plurality of text segment data objects comprises (i) receiving a plurality of candidate categorical identifiers and a respective plurality of categorical descriptions, (ii) selecting, for the plurality of text segment data objects, one or more model-assigned categorical identifiers from the plurality of candidate categorical identifiers, and (iii) generating one or more categorical predictions based on the selected one or more model-assigned categorical identifiers.

In some embodiments, a generative machine learning model is configured to perform a multi-label binary classification comprising selecting one or more categorical identifiers from a plurality of candidate categorical identifiers and assigning the one or more categorical identifiers to one or more text segment data objects associated with a document data object. In some embodiments, a generative machine learning model comprises a LLM. The LLM may be any general LLM or any pre-trained and fine-tuned generative model, such as a generative pre-trained transformer. For example, a generative machine learning model may be pre-trained on a relatively broad-scoped dataset (e.g., than that of a fine-tuning dataset) usable by the generative machine learning model to learn general functionalities that may help the generative machine learning model perform a specific task upon fine-tuning. In some embodiments, a generative machine learning model may be fine-tuned on medical text data, such as electronic health record (EHR) or claims data from electronic medical records (EMR) or databases.

In some embodiments, assigning a model-assigned categorical identifier comprises either generating or receiving one or more prompt commands and providing the one or more prompt commands to a generative machine learning model. The one or more prompt commands may instruct the generative machine learning model to assign categorical identifiers (model-assigned categorical identifiers) to one or more text segment data objects of a document data object.

In some embodiments, a prompt command describes instructions for initiating in-context learning (ICL) with a generative machine learning model. ICL may comprise a generative machine learning model learning to generate relevant and accurate responses based on a prompt command. A prompt command may comprise a context to analyze comprising one or more examples, one or more analysis inputs, and a task-specific instruction to follow and repeat based on the one or more examples and the one or more analysis inputs (e.g., assigning model-assigned categorical identifiers). Via a command prompt, a generative machine learning model may adapt its knowledge after each instruction execution and generate a suitable output.

FIG. 6 depicts an operational example of a prompt command 600 for assigning model-assigned categorical identifiers to text segment data objects in accordance with some embodiments of the present disclosure. As depicted in FIG. 6, prompt command 600 comprises an example 602, analysis inputs 604, and task-specific instructions 606. Example 602 comprises a document data object or one or more text segment data objects, and categorical identifiers assigned to the document data object or one or more text segment data objects. In some embodiments, prompt command 600 is provided to a generative machine learning model for generating prediction outputs.

Returning to FIG. 5, in some embodiments, at step/operation 506, the document analysis computing entity 106 identifies, using the generative machine learning model, one or more evidence text portions from the plurality of text segment data objects. In some embodiments, an evidence text portion describes a part of a text segment data object comprising a basis relied on by a generative machine learning model for assigning one or more categorical identifiers to the text segment data object or a document data object comprising the text segment data object. Evidence text portions may be identified from a text segment data object based on an attribution of the evidence text portions to a selection of one or more model-assigned categorical identifiers (from a plurality of candidate categorical identifiers) for assignment to the text segment data object or document data object. In some embodiments, the one or more evidence text portions may be provided along with a classification generated for the document data object.

In some embodiments, identifying evidence text portions comprises either generating or receiving one or more prompt commands and providing the one or more prompt commands to a generative machine learning model. The one or more prompt commands may instruct the generative machine learning model to extract text from one or more text segment data objects that contribute to assignment of one or more categorical identifiers to the one or more text segment data objects. In some embodiments, one or more prompt commands comprising one or more examples, one or more analysis inputs, and an instruction to follow (e.g., identifying evidence text portions) and repeat based on the one or more examples and the one or more analysis inputs are provided to a generative machine learning model. Based on the one or more prompt commands, the generative machine learning model may generate an output, e.g., identify one or more evidence text portions.

In some embodiments, a generative machine learning model may be prompted, via one or more prompt commands, to extract evidence text portions that contribute to assignments of model-assigned categorical identifiers to a plurality of text segment data objects by the generative machine learning model. In one example embodiment, the one or more prompt commands comprise prompt engineering strategies including few-shot demonstration, instruction induction, and self-consistency. Few-shot demonstration may comprise providing examples of a categorical identifier-evidence text portion pair labeled by expert users. Instruction induction may comprise task-specific instructions based on few-shot demonstration examples. Self-consistency may comprise repetitive performance of an instructed task and selecting an output via majority vote.

FIG. 7 depicts an operational example of a prompt command 700 for identifying evidence text portions from text segment data objects in accordance with some embodiments of the present disclosure. As depicted in FIG. 7, prompt command 700 comprises analysis inputs 702, task-specific instructions 704, and examples 706. Examples 706 comprise correct and incorrect instances of categorical identifier assignments based on evidence text portions. In some embodiments, prompt command 700 is provided to a generative machine learning model for identifying evidence text portions from text segment data objects for supporting assignment of model-assigned categorical identifiers by the generative machine learning model.

Returning to FIG. 5, in some embodiments, at step/operation 508, the document analysis computing entity 106 generates, using a verifier machine learning model, one or more evidence predictions on respective ones of the one or more evidence text portions. According to various embodiments of the present disclosure, the one or more evidence predictions may be used to refine or filter the plurality of model-assigned categorical identifiers (assigned to the plurality of text segment data objects associated with the document data object by the generative machine learning model) to generate a final classification for the document data object. That is, the generative machine learning model may over-assign categorical identifiers, resulting in high recall (or an amount of positive classifications) but low precision. To increase precision, a verifier machine learning model may be trained to generate evidence predictions on evidence text portions based on how well the evidence text portions are able to correctly predict a classification of a document data object.

In some embodiments, an evidence prediction describes an output generated by a verifier machine learning model representative of an accuracy or predictive quality of an evidence text portion with respect to a classification of a document data object. Evidence predictions may be generated for evidence text portions associated with a plurality of model-assigned categorical identifiers and used to refine or filter the plurality of model-assigned categorical identifiers. For example, evidence predictions may confirm or verify the model-assigned categorical identifiers. In some embodiments, a verifier machine learning model may be trained to generate evidence predictions on evidence text portions to evaluate bases for assigning certain categorical identifiers to text segment data objects or a document data object by a generative machine learning model. According to various embodiments of the present disclosure, the document analysis computing entity 106 is configured to (i) generate, using a verifier machine learning model, one or more evidence predictions on respective ones of one or more evidence text portions associated with a plurality of model-assigned categorical identifiers, wherein the plurality of model-assigned categorical identifiers are assigned to a plurality of text segment data objects associated with a document data object, (ii) generate a filter set of the plurality of model-assigned categorical identifiers based on the one or more evidence predictions, and (iii) generate one or more classifications for the document data object based on the filter set. In some embodiments, the document analysis computing entity 106 is further configured to provide the one or more evidence text portions along with the one or more classifications based on the one or more evidence predictions.

In some embodiments, a verifier machine learning model describes parameters, hyperparameters, and/or defined operations of a machine learning model that is configured to generate evidence predictions on evidence text portions. A verifier machine learning model may be trained to generate evidence predictions on evidence text portions to evaluate bases for assigning certain categorical identifiers to text segment data objects or a document data object by a generative machine learning model. In some embodiments, a verifier machine learning model is configured and/or used to generate one or more evidence predictions on one or more evidence text portions based on one or more weights trained on ground truth data comprising one or more model-generated training labels and/or one or more expert-labeled document data objects. In some embodiments, training one or more weights of a verifier machine learning model comprises determining one or more loss values based on a difference between one or more evidence predictions generated by the verifier machine learning and one or more model-generated training labels or one or more expert-labeled document data objects. In some embodiments, one or more categorical identifier-evidence text portion pairs may be used in combination with one or more model-generated training labels and one or more expert-labeled document data objects to generate one or more weights of a verifier machine learning model configured to generate one or more evidence predictions on one or more evidence text portions. Generating evidence predictions is described in further detail with respect to the description of FIG. 8.

In some embodiments, a categorical identifier-evidence text portion pair describes a grouping of a categorical identifier with an evidence text portion. According to various embodiments of the present disclosure, a generative machine learning model is configured to identify one or more evidence text portions from one or more text segment data objects associated with respective one or more categorical identifiers. Each of the identified one or more evidence text portions may thereby form a categorical identifier-evidence text portion pair with the respective one or more categorical identifiers.

FIG. 8 is a flowchart diagram of an example process for generating evidence predictions in accordance with some embodiments of the present disclosure.

In some embodiments, the process 800 begins at step/operation 802 when the document analysis computing entity 106 receives a plurality of categorical identifier-evidence text portion pairs. The plurality of categorical identifier-evidence text portion pairs may comprise a plurality of evidence text portions and a plurality of candidate categorical identifiers. The plurality of evidence text portions may be determined from a plurality of text segment data objects by a generative machine learning model as supporting a respective plurality of classifications associated with the plurality of candidate categorical identifiers.

In some embodiments, at step/operation 804, the document analysis computing entity 106 generates a plurality of evidence scores for respective ones of the plurality of categorical identifier-evidence text portion pairs. In some embodiments, an evidence score describes a measurement or value representative of how well an evidence text portion is able to characterize or support an assignment of a particular categorical identifier, e.g., to a text segment data object or a document data object. For example, an evidence score may be representative of a degree of attribution of an evidence text portion to a classification (e.g., of a document data object). As such, evidence scores may be used to identify evidence text portions that are most relevant to a classification of a document data object with respect to a particular model-assigned categorical identifier. According to various embodiments of the present disclosure, an evidence score may be generated for each of one or more evidence text portions associated with a categorical identifier-evidence text portion pair by a verifier machine learning model based on evidence predictions on respective ones of the one or more evidence text portions. In some embodiments, an evidence score may be generated by row max pooling one or more evidence predictions associated with one or more categorical identifier-evidence text portion pairs comprising a given categorical identifier. In some embodiments, evidence text portions comprising highest evidence scores may be identified and provided along with one or more classifications of a document data object, e.g., for the purposes of explainability or providing reasoning for the one or more classifications.

In some embodiments, at step/operation 806, the document analysis computing entity 106 determines whether one or more model-assigned categorical identifiers are correctly assigned to the plurality of text segment data objects based on the plurality of evidence scores. The one or more model-assigned categorical identifiers may comprise categorical identifiers that are assigned to a plurality of text segment data objects by the generative machine learning model that determined the plurality of evidence text portions associated with the categorical identifier-evidence text portion pairs from the plurality of text segment data objects. For example, the one or more model-assigned categorical identifiers may be determined to be corrected assigned to the plurality of text segment data objects based on the plurality of evidence scores exceeding an evidence score threshold.

Returning to FIG. 5, in some embodiments, at step/operation 510, the document analysis computing entity 106 generates a filter set of the plurality of model-assigned categorical identifiers based on the one or more evidence predictions. In some embodiments, a filter set describes a set of model-assigned categorical identifiers selected from a plurality of model-assigned categorical identifiers based on one or more evidence predictions generated by a verifier machine learning model. A filter set may be generated to refine (e.g., improve precision) a plurality of model-assigned categorical identifiers (e.g., high recall) that are assigned to text segment data objects of a document data object by a generative machine learning model.

In some embodiments, at step/operation 512, the document analysis computing entity 106 generates one or more classifications of the document data object based on the filter set. In some embodiments, the one or more evidence text portions may be provided along with a classification generated for the document data object based on the one or more evidence predictions.

Figure 9:
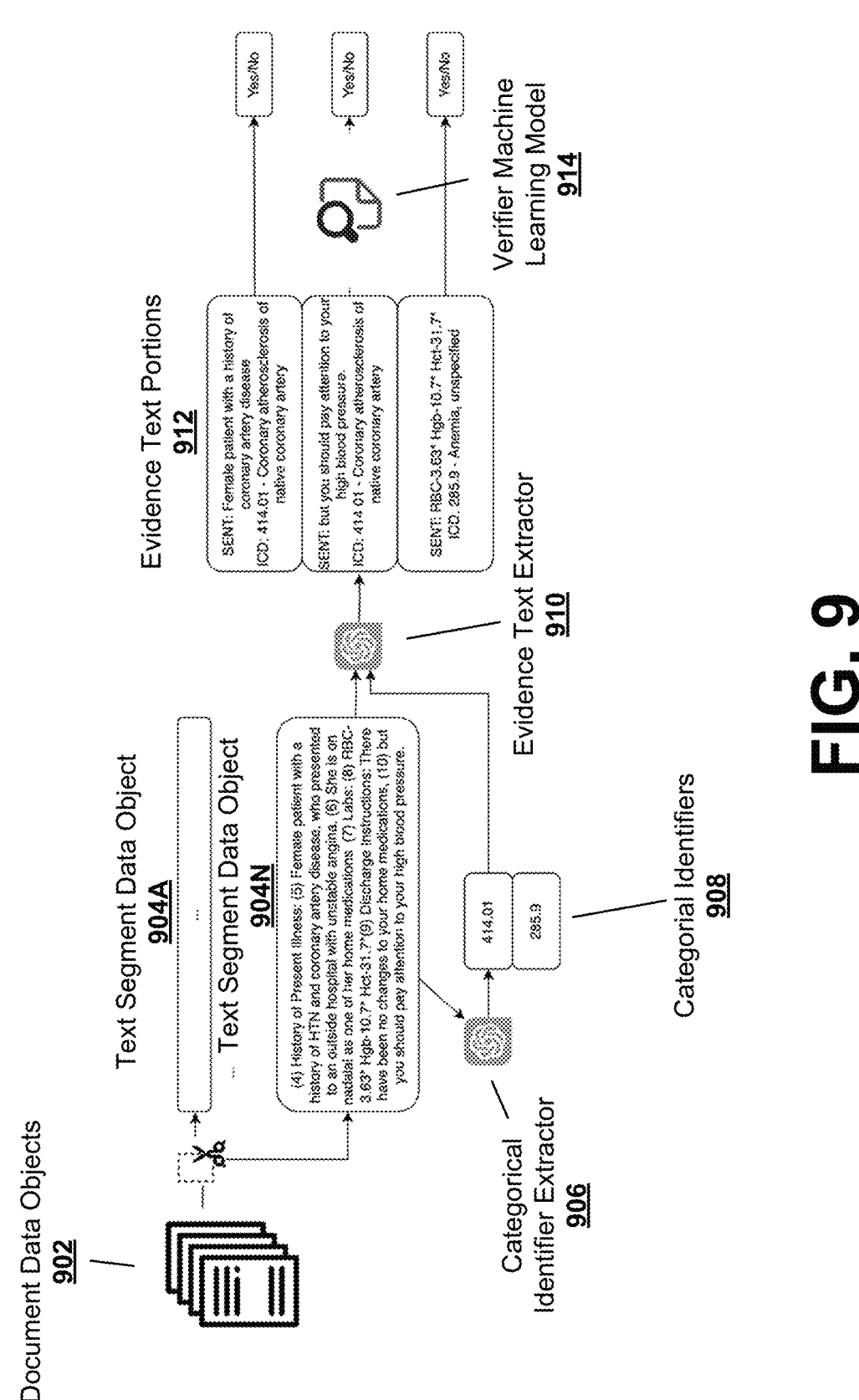
FIG. 9 depicts an operational example of a classification system architecture in accordance with some embodiments of the present disclosure.

In some embodiments, an operational example of a classification system architecture 900 is depicted in FIG. 9. As depicted in FIG. 9, in some embodiments, document data objects 902 may be segmented into text segment data objects 904A-904N. FIG. 9 further depicts categorical identifiers 908 identified or extracted from text segment data objects 904A-904N by categorical identifier extractor 906. In some embodiments, the categorical identifier extractor 906 comprises a generative machine learning model.

Evidence text extractor 910 may determine evidence text portions 912 from text segment data objects 904A-904N associated with categorical identifiers 908. In some embodiments, evidence text extractor 910 comprises a generative machine learning model, e.g., related to the categorical identifier extractor 906. The evidence text portions 912 may be analyzed by a verifier machine learning model 914 to generate evidence predictions which may confirm or verify the categorical identifiers 908 for refining or filtering the categorical identifiers to generate one or more classifications for the document data objects 902. In some embodiments, evidence text portions 912 may be provided along with the one or more classifications to support the one or more classification.

Figure 10:
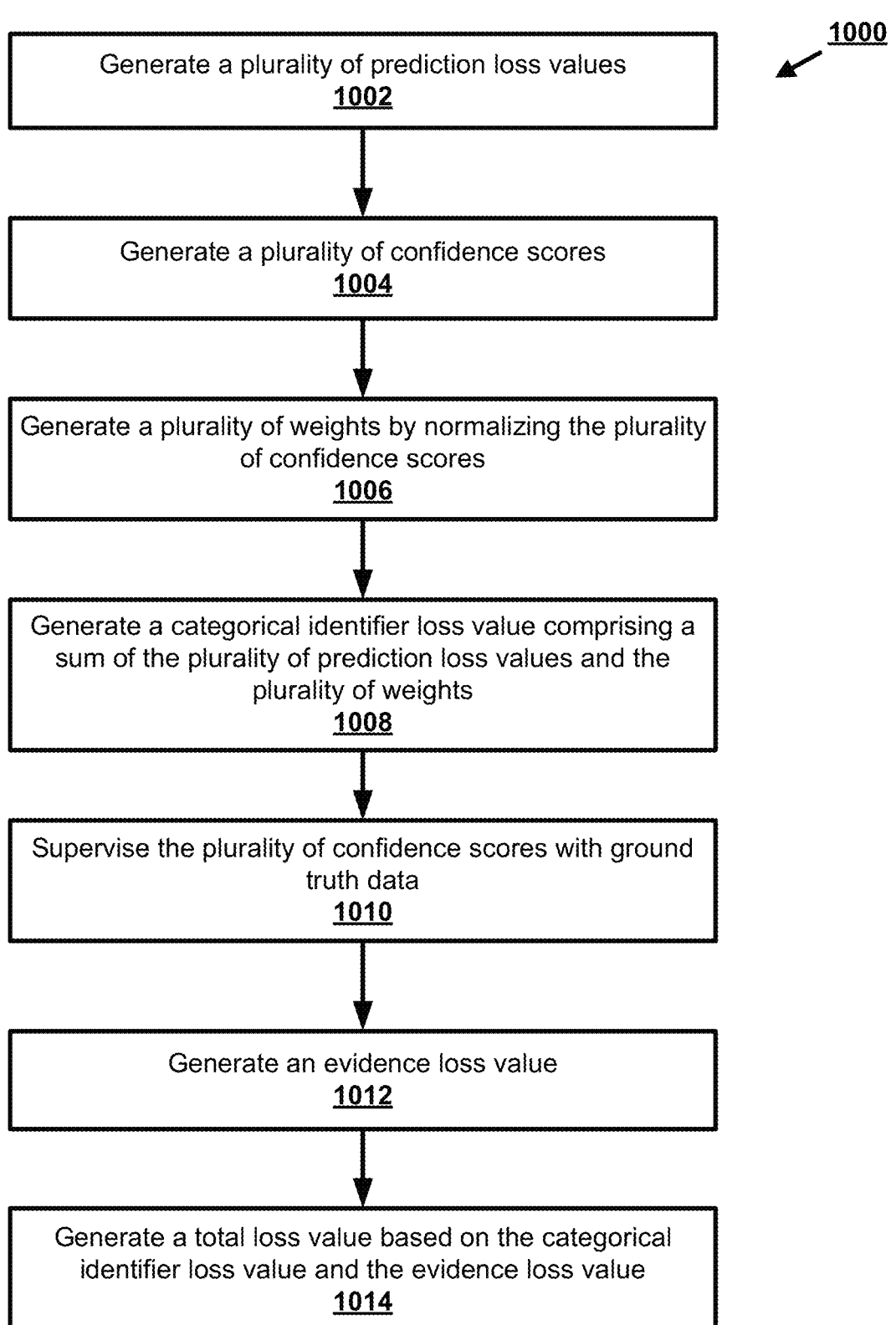
FIG. 10 is a flowchart diagram of an example process for training a verifier machine learning model in accordance with some embodiments of the present disclosure.

FIG. 10 is a flowchart diagram of an example process for training a verifier machine learning model in accordance with some embodiments of the present disclosure.

Training a verifier machine learning model may comprise determining and evaluating a verifier machine learning model based on various loss values. In some embodiments, a loss value describes a numerical value representative of how well a machine learning model is able to correctly generate a given prediction. For example, low loss values may be representative of accurate predictions, while conversely, higher loss values may be representative of incorrect predictions. As such, a machine learning model may be trained to minimize loss values for predictions generated by the machine learning model. A loss value may be determined based on supervision or validation of one or more confidence scores associated with one or more predictions with ground truth data comprising one or more model-generated training labels and/or one or more expert-labeled document data objects.

In some embodiments, the process 1000 begins at step/operation 1002 when the document analysis computing entity 106 generates a plurality of prediction loss values associated with a plurality of candidate evidence text portions identified from one or more documents for one or more categorical identifiers. The plurality of prediction loss values may be generated by (a) normalizing a plurality of evidence predictions generated by a verifier machine learning model and (b) determining a cross-entropy of the normalized plurality of evidence predictions. In some embodiments, normalizing the plurality of evidence predictions may comprise applying an activation function, such as Softmax.

In some embodiments, at step/operation 1004, the document analysis computing entity 106 generates a plurality of confidence scores by row max pooling the plurality of evidence predictions.

In some embodiments, at step/operation 1006, the document analysis computing entity 106 generates a plurality of weights by normalizing the plurality of confidence scores. Normalizing the plurality of weights may comprise applying an activation function, such as Softmax.

In some embodiments, at step/operation 1008, the document analysis computing entity 106 generates a categorical identifier loss value comprising a sum based on the plurality of prediction loss values and the plurality of weights. In one example embodiment, a categorical identifier loss value may be generated by the following:

$$l_{cat\_identifier} = \sum_{k} \sum_{j} w_{k,j} l_{k,j} \qquad \text{Equation 1}$$

According to Equation 1, $l_{cat\_identifier}$ may represent a categorical identifier loss, $w_{k,j}$ may represent weights for k documents and j candidate evidence text portions, and $l_{k,j}$ may represent prediction loss values for k documents and j candidate evidence text portions.

In some embodiments, at step/operation 1010, the document analysis computing entity 106 supervises or validates the plurality of confidence scores with ground truth data comprising one or more model-generated training labels and/or one or more expert-labeled document data objects, In some embodiments, a model-generated training label describes training data comprising a classification that is generated by a generative machine learning model. For example, a model-generated training label may comprise a model-assigned categorical identifier that is tagged or identified with a text segment data object by the generative machine learning model.

In some embodiments, an expert-labeled document data object describes a document data object, one or more text segment data objects, or generally text data objects that is/are labeled with one or more categorical identifiers by an expert user.

In some embodiments, at step/operation 1012, the document analysis computing entity 106 generates an evidence loss value. The evidence loss value may be generated by (a) normalizing the supervised/validated plurality of confidence scores based on a sigmoid function and (b) determining a binary cross-entropy of the normalized and supervised/validated plurality of confidence scores.

In some embodiments, at step/operation 1014, the document analysis computing entity 106 generates a total loss value based on the categorical identifier loss value and the evidence loss value. The total loss value may be used to update one or more weights of a verifier machine learning model for generating evidence predictions.

Figure 11:
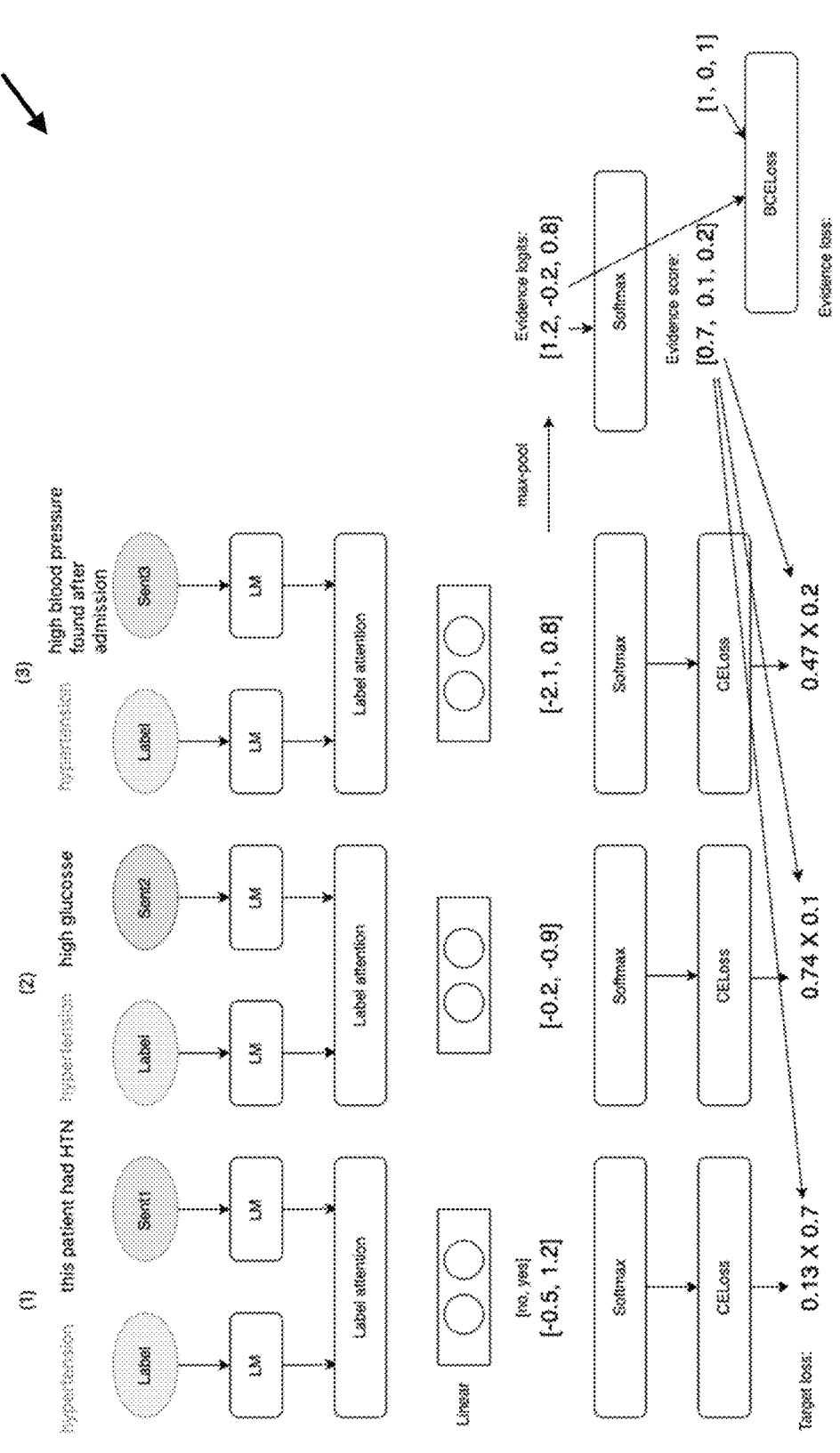
FIG. 11 depicts an operational example of a verifier machine learning model for determining loss values in accordance with some embodiments of the present disclosure.

FIG. 11 depicts an operational example of a verifier machine learning model 1100 for determining loss values in accordance with some embodiments of the present disclosure. As depicted in FIG. 11, a plurality of candidate evidence text portions for a given categorical identifier are provided for generation of a plurality of evidence predictions. The plurality of evidence predictions is used to determine loss values as described with reference to the description of FIG. 10.

Accordingly, as described above, various embodiments of the present disclosure make important technical contributions to improving classification accuracy of document classification systems by configuring a generative machine learning model to identify one or more evidence text portions comprising one or more bases relied on by the generative machine learning model for assigning a plurality of categorical identifiers to a plurality of text segment data objects associated with a document data object, and verifying the one or more evidence text portions with a verifier machine learning model to generate one or more classifications of the document data object and provide the one or more verified evidence text portions along with the one or more classifications. This approach improves training speed and training efficiency of training predictive machine learning models. It is well-understood in the relevant art that there is typically a tradeoff between predictive accuracy and training speed, such that it is trivial to improve training speed by reducing predictive accuracy. Thus, the challenge is to improve training speed without sacrificing predictive accuracy through innovative machine learning model architectures. Accordingly, techniques that improve predictive accuracy without harming training speed, such as the techniques described herein, enable improving training speed given a constant predictive accuracy. In doing so, the techniques described herein improve efficiency and speed of training predictive machine learning models, thus reducing the number of computational operations needed and/or the amount of training data entries needed to train predictive machine learning models. Accordingly, the techniques described herein improve the computational efficiency, storage-wise efficiency, and/or speed of training machine learning models.

Some techniques of the present disclosure enable the generation of classification outputs that may be used to initiate one or more predictive actions to achieve real-world effects. The techniques of the present disclosure may be used, applied, and/or otherwise leveraged to generate a verifier machine learning model, which may help in the classification of document data objects. The usage of a generative machine learning model with a verifier machine learning model of the present disclosure may be leveraged to initiate the performance of various computing tasks that improve the performance of a computing system (e.g., a computer itself, etc.) with respect to various predictive actions performed by the document analysis computing entity 106, such as for the classification of long documents, and/or the like. Example predictive actions may include the generation of a filter set of a plurality of model-assigned categorical identifiers one or more classifications of a document data object based on the filter set.

In some examples, the computing tasks may include predictive actions that may be based on a prediction domain. A prediction domain may include any environment in which computing systems may be applied to achieve real-word insights, such as predictions (e.g., abstractive summaries, predictive intents, etc.), and initiate the performance of computing tasks, such as predictive actions e.g., updating user preferences, providing account information, cancelling an account, adding an account, etc.) to act on the real-world insights. These predictive actions may cause real-world changes, for example, by controlling a hardware component, providing alerts, interactive actions, and/or the like.

Examples of prediction domains may include financial systems, clinical systems, autonomous systems, robotic systems, and/or the like. Predictive actions in such domains may include the initiation of automated instructions across and between devices, automated notifications, automated scheduling operations, automated precautionary actions, automated security actions, automated data processing actions, automated data compliance actions, automated data access enforcement actions, automated adjustments to computing and/or human data access management, and/or the like.

In some embodiments, the classification techniques of process 1000 are applied to initiate the performance of one or more predictive actions. A predictive action may depend on the prediction domain. In some examples, the document analysis computing entity 106 may leverage the classification techniques to assist a generative machine learning model with a verifier machine learning model to initiate the classification of documents, and/or any other operations for interpreting complex text corpora.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

VII. EXAMPLES

Example 1. A computer-implemented method comprising: generating, by one or more processors, a plurality of text segment data objects associated with a document data object; assigning, by the one or more processors and using a first machine learning model, a plurality of model-assigned categorical identifiers to the plurality of text segment data objects; identifying, by the one or more processors and using the first machine learning model, one or more evidence text portions from the plurality of text segment data objects, the one or more evidence text portions comprising one or more bases relied on by the first machine learning model for the assigning; generating, by the one or more processors and using a second machine learning model, one or more evidence predictions on respective ones of the one or more evidence text portions; generating, by the one or more processors, a filter set of the plurality of model-assigned categorical identifiers based on the one or more evidence predictions; and generating, by the one or more processors, one or more classifications of the document data object based on the filter set.

Example 2. The computer-implemented method of any of the preceding examples, wherein the first machine learning model comprises a generative machine learning model.

Example 3. The computer-implemented method of any of the preceding examples, wherein the second machine learning model comprises a verifier machine learning model.

Example 4. The computer-implemented method of any of the preceding examples, wherein assigning the plurality of model-assigned categorical identifiers to the plurality of text segment data objects further comprises: receiving a plurality of candidate categorical identifiers and a respective plurality of categorical descriptions; selecting, for the plurality of text segment data objects, one or more of the plurality of candidate categorical identifiers; and generating one or more categorical predictions based on the selected one or more model-assigned categorical identifiers.

Example 5. The computer-implemented method of any of the preceding examples further comprising: generating, using the first machine learning model, one or more categorical identifier-evidence text portion pairs; and generating the one or more evidence predictions based on one or more weights trained on the one or more categorical identifier-evidence text portion pairs and ground truth data comprising one or more model-generated training labels or one or more expert-labeled document data objects.

Example 6. The computer-implemented method of any of the preceding examples, wherein generating the one or more evidence predictions further comprises: receiving a plurality of categorical identifier-evidence text portion pairs, the plurality of categorical identifier-evidence text portion pairs comprising the plurality of evidence text portions and a plurality of candidate categorical identifiers; generating a plurality of evidence scores for respective ones of the plurality of categorical identifier-evidence text portion pairs; and determining whether the plurality of model-assigned categorical identifiers are correctly assigned to the plurality of text segment data objects based on the plurality of evidence scores.

Example 7. The computer-implemented method of any of the preceding examples further comprising: determining one or more loss values based on a difference between the one or more evidence predictions and one or more model-generated training labels or one or more expert-labeled document data objects; and training one or more weights associated with the second machine learning model based on the one or more loss values.

Example 8. The computer-implemented method of any of the preceding examples further comprising training the second machine learning model by: generating a plurality of prediction loss values by (a) normalizing the plurality of evidence predictions and (b) determining a cross-entropy of the normalized plurality of evidence predictions; generating a plurality of confidence scores by row max pooling the plurality of evidence predictions; generating a plurality of weights by normalizing the plurality of confidence scores; generating a categorical identifier loss value comprising a sum based on the plurality of prediction loss values and the plurality of weights; validating the plurality of confidence scores with ground truth data; generating an evidence loss value by (a) normalizing the validated plurality of confidence scores and (b) determining a binary cross-entropy of the normalized and validated plurality of confidence scores; and generating a total loss value based on the categorical identifier loss value and the evidence loss value.

Example 9. A computing system comprising memory and one or more processors communicatively coupled to the memory, the one or more processors configured to: generate a plurality of text segment data objects associated with a document data object; assign, using a first machine learning model, a plurality of model-assigned categorical identifiers to the plurality of text segment data objects; identify, using the first machine learning model, one or more evidence text portions from the plurality of text segment data objects, the one or more evidence text portions comprising one or more bases relied on by the first machine learning model for the assigning; generate, using a second machine learning model, one or more evidence predictions on respective ones of the one or more evidence text portions; generate a filter set of the plurality of model-assigned categorical identifiers based on the one or more evidence predictions; and generate one or more classifications of the document data object based on the filter set.

Example 10. The computing system of any of the preceding examples, wherein the first machine learning model comprises a generative machine learning model.

Example 11. The computing system of any of the preceding examples, wherein the second machine learning model comprises a verifier machine learning model.

Example 12. The computing system of any of the preceding examples, wherein the one or more processors are further configured to: receive a plurality of candidate categorical identifiers and a respective plurality of categorical descriptions; select, for the plurality of text segment data objects, one or more of the plurality of candidate categorical identifiers; and generate one or more categorical predictions based on the selected one or more model-assigned categorical identifiers.

Example 13. The computing system of any of the preceding examples, wherein the one or more processors are further configured to: generate, using the first machine learning model, one or more categorical identifier-evidence text portion pairs; and generate the one or more evidence predictions based on one or more weights trained on the one or more categorical identifier-evidence text portion pairs and ground truth data comprising one or more model-generated training labels or one or more expert-labeled document data objects.

Example 14. The computing system of any of the preceding examples, wherein the one or more processors are further configured to: receive a plurality of categorical identifier-evidence text portion pairs, the plurality of categorical identifier-evidence text portion pairs comprising the plurality of evidence text portions and a plurality of candidate categorical identifiers; generate a plurality of evidence scores for respective ones of the plurality of categorical identifier-evidence text portion pairs; and determine whether the plurality of model-assigned categorical identifiers are correctly assigned to the plurality of text segment data objects based on the plurality of evidence scores.

Example 15. The computing system of any of the preceding examples, wherein the one or more processors are further configured to: determine one or more loss values based on a difference between the one or more evidence predictions and one or more model-generated training labels or one or more expert-labeled document data objects; and train one or more weights associated with the second machine learning model based on the one or more loss values.

Example 16. The computing system of any of the preceding examples, wherein the one or more processors are further configured to: generate a plurality of prediction loss values by (a) normalizing the plurality of evidence predictions and (b) determining a cross-entropy of the normalized plurality of evidence predictions; generate a plurality of confidence scores by row max pooling the plurality of evidence predictions; generate a plurality of weights by normalizing the plurality of confidence scores; generate a categorical identifier loss value comprising a sum based on the plurality of prediction loss values and the plurality of weights; validate the plurality of confidence scores with ground truth data; generating an evidence loss value by (a) normalizing the validated plurality of confidence scores and (b) determining a binary cross-entropy of the normalized and validated plurality of confidence scores; and generate a total loss value based on the categorical identifier loss value and the evidence loss value.

Example 17. One or more non-transitory computer-readable storage media including instructions that, when executed by one or more processors, cause the one or more processors to: generate a plurality of text segment data objects associated with a document data object; assign, using a first machine learning model, a plurality of model-assigned categorical identifiers to the plurality of text segment data objects; identify, using the first machine learning model, one or more evidence text portions from the plurality of text segment data objects, the one or more evidence text portions comprising one or more bases relied on by the first machine learning model for the assigning; generate, using a second machine learning model, one or more evidence predictions on respective ones of the one or more evidence text portions; generate a filter set of the plurality of model-assigned categorical identifiers based on the one or more evidence predictions; and generate one or more classifications of the document data object based on the filter set.

Example 18. The one or more non-transitory computer-readable storage media of any of the preceding examples, wherein the first machine learning model comprises a generative machine learning model.

Example 19. The one or more non-transitory computer-readable storage media of any of the preceding examples, wherein the second machine learning model comprises a verifier machine learning model.

Example 20. The one or more non-transitory computer-readable storage media of any of the preceding examples, further including instructions that, when executed by one or more processors, cause the one or more processors to: receive a plurality of candidate categorical identifiers and a respective plurality of categorical descriptions; select, for the plurality of text segment data objects, one or more of the plurality of candidate categorical identifiers; and generate one or more categorical predictions based on the selected one or more model-assigned categorical identifiers.

Example 21. The one or more non-transitory computer-readable storage media of any of the preceding examples, further including instructions that, when executed by one or more processors, cause the one or more processors to: generate, using the first machine learning model, one or more categorical identifier-evidence text portion pairs; and generate the one or more evidence predictions based on one or more weights trained on the one or more categorical identifier-evidence text portion pairs and ground truth data comprising one or more model-generated training labels or one or more expert-labeled document data objects.

Example 22. The one or more non-transitory computer-readable storage media of any of the preceding examples, further including instructions that, when executed by one or more processors, cause the one or more processors to: receive a plurality of categorical identifier-evidence text portion pairs, the plurality of categorical identifier-evidence text portion pairs comprising the plurality of evidence text portions and a plurality of candidate categorical identifiers; generate a plurality of evidence scores for respective ones of the plurality of categorical identifier-evidence text portion pairs; and determine whether the plurality of model-assigned categorical identifiers are correctly assigned to the plurality of text segment data objects based on the plurality of evidence scores.

Example 23. The one or more non-transitory computer-readable storage media of any of the preceding examples, further including instructions that, when executed by one or more processors, cause the one or more processors to: determine one or more loss values based on a difference between the one or more evidence predictions and one or more model-generated training labels or one or more expert-labeled document data objects; and train one or more weights associated with the second machine learning model based on the one or more loss values.

Example 24. The one or more non-transitory computer-readable storage media of any of the preceding examples, further including instructions that, when executed by one or more processors, cause the one or more processors to: generate a plurality of prediction loss values by (a) normalizing the plurality of evidence predictions and (b) determining a cross-entropy of the normalized plurality of evidence predictions; generate a plurality of confidence scores by row max pooling the plurality of evidence predictions; generate a plurality of weights by normalizing the plurality of confidence scores; generate a categorical identifier loss value comprising a sum based on the plurality of prediction loss values and the plurality of weights; validate the plurality of confidence scores with ground truth data; generating an evidence loss value by (a) normalizing the validated plurality of confidence scores and (b) determining a binary cross-entropy of the normalized and validated plurality of confidence scores; and generate a total loss value based on the categorical identifier loss value and the evidence loss value.

The invention claimed is:

1. A computer-implemented method comprising:

generating, by one or more processors, a plurality of text segment data objects associated with a document data object;

assigning, by the one or more processors and using a first machine learning model, a plurality of model-assigned categorical identifiers to the plurality of text segment data objects;

identifying, by the one or more processors and using the first machine learning model, one or more evidence text portions from the plurality of text segment data objects, the one or more evidence text portions comprising one or more bases relied on by the first machine learning model for the assigning;

generating, by the one or more processors and using a second machine learning model, one or more evidence predictions on respective ones of the one or more evidence text portions;

generating, by the one or more processors, a filter set of the plurality of model-assigned categorical identifiers based on the one or more evidence predictions; and generating, by the one or more processors, one or more classifications of the document data object based on the filter set.

2. The computer-implemented method of claim 1, wherein the first machine learning model comprises a generative machine learning model.

3. The computer-implemented method of claim 1, wherein the second machine learning model comprises a verifier machine learning model.

4. The computer-implemented method of claim 1, wherein assigning the plurality of model-assigned categorical identifiers to the plurality of text segment data objects further comprises:

receiving a plurality of candidate categorical identifiers and a respective plurality of categorical descriptions;

selecting, for the plurality of text segment data objects, one or more of the plurality of candidate categorical identifiers; and generating one or more categorical predictions based on the selected one or more model-assigned categorical identifiers.

5. The computer-implemented method of claim 1 further comprising:

generating, using the first machine learning model, one or more categorical identifier-evidence text portion pairs; and generating the one or more evidence predictions based on one or more weights trained on the one or more categorical identifier-evidence text portion pairs and ground truth data comprising one or more model-generated training labels or one or more expert-labeled document data objects.

6. The computer-implemented method of claim 1, wherein generating the one or more evidence predictions further comprises:

receiving a plurality of categorical identifier-evidence text portion pairs, the plurality of categorical identifier-evidence text portion pairs comprising the plurality of evidence text portions and a plurality of candidate categorical identifiers;

generating a plurality of evidence scores for respective ones of the plurality of categorical identifier-evidence text portion pairs; and determining whether the plurality of model-assigned categorical identifiers are correctly assigned to the plurality of text segment data objects based on the plurality of evidence scores.

7. The computer-implemented method of claim 1 further comprising:

determining one or more loss values based on a difference between the one or more evidence predictions and one or more model-generated training labels or one or more expert-labeled document data objects; and training one or more weights associated with the second machine learning model based on the one or more loss values.

8. The computer-implemented method of claim 1 further comprising training the second machine learning model by:

generating a plurality of prediction loss values by (a) normalizing the plurality of evidence predictions and (b) determining a cross-entropy of the normalized plurality of evidence predictions;

generating a plurality of confidence scores by row max pooling the plurality of evidence predictions;

generating a plurality of weights by normalizing the plurality of confidence scores;

generating a categorical identifier loss value comprising a sum based on the plurality of prediction loss values and the plurality of weights;

validating the plurality of confidence scores with ground truth data;

generating an evidence loss value by (a) normalizing the validated plurality of confidence scores and (b) determining a binary cross-entropy of the normalized and validated plurality of confidence scores; and generating a total loss value based on the categorical identifier loss value and the evidence loss value.

9. A computing system comprising memory and one or more processors communicatively coupled to the memory, the one or more processors configured to:

generate a plurality of text segment data objects associated with a document data object;

assign, using a first machine learning model, a plurality of model-assigned categorical identifiers to the plurality of text segment data objects;

identify, using the first machine learning model, one or more evidence text portions from the plurality of text segment data objects, the one or more evidence text portions comprising one or more bases relied on by the first machine learning model for the assigning;

generate, using a second machine learning model, one or more evidence predictions on respective ones of the one or more evidence text portions;

generate a filter set of the plurality of model-assigned categorical identifiers based on the one or more evidence predictions; and generate one or more classifications of the document data object based on the filter set.

10. The computing system of claim 9, wherein the first machine learning model comprises a generative machine learning model.

11. The computing system of claim 9, wherein the second machine learning model comprises a verifier machine learning model.

12. The computing system of claim 9, wherein the one or more processors are configured to:

generate, using the first machine learning model, one or more categorical identifier-evidence text portion pairs; and generate the one or more evidence predictions based on one or more weights trained on the one or more categorical identifier-evidence text portion pairs and ground truth data comprising one or more model-generated training labels or one or more expert-labeled document data objects.

13. The computing system of claim 9, wherein the one or more processors are further configured to:

receive a plurality of categorical identifier-evidence text portion pairs, the plurality of categorical identifier-evidence text portion pairs comprising the plurality of evidence text portions and a plurality of candidate categorical identifiers;

generate a plurality of evidence scores for respective ones of the plurality of categorical identifier-evidence text portion pairs; and determine whether the plurality of model-assigned categorical identifiers are correctly assigned to the plurality of text segment data objects based on the plurality of evidence scores.

14. The computing system of claim 9, wherein the one or more processors are further configured to:

determine one or more loss values based on a difference between the one or more evidence predictions and one or more model-generated training labels or one or more expert-labeled document data objects; and generate one or more weights associated with the second machine learning model based on the one or more loss values.

15. The computing system of claim 9, wherein the one or more processors are further configured to:

generate a plurality of prediction loss values by (a) normalizing the plurality of evidence predictions and (b) determining a cross-entropy of the normalized plurality of evidence predictions;

generate a plurality of confidence scores by row max pooling the plurality of evidence predictions;

generate a plurality of weights by normalizing the plurality of confidence scores;

generate a categorical identifier loss value comprising a sum based on the plurality of prediction loss values and the plurality of weights;

validate the plurality of confidence scores with ground truth data;

generate an evidence loss value by (a) normalizing the validated plurality of confidence scores and (b) determining a binary cross-entropy of the normalized and validated plurality of confidence scores; and generate a total loss value based on the categorical identifier loss value and the evidence loss value.

16. One or more non-transitory computer-readable storage media including instructions that, when executed by one or more processors, cause the one or more processors to:

generate a plurality of text segment data objects associated with a document data object;

assign, using a first machine learning model, a plurality of model-assigned categorical identifiers to the plurality of text segment data objects;

identify, using the first machine learning model, one or more evidence text portions from the plurality of text segment data objects, the one or more evidence text portions comprising one or more bases relied on by the first machine learning model for the assigning;

generate, using a second machine learning model, one or more evidence predictions on respective ones of the one or more evidence text portions;

generate a filter set of the plurality of model-assigned categorical identifiers based on the one or more evidence predictions; and generate one or more classifications of the document data object based on the filter set.

17. The one or more non-transitory computer-readable storage media of claim 16, further including instructions that, when executed by the one or more processors, cause the one or more processors to:

generate, using the first machine learning model, one or more categorical identifier-evidence text portion pairs; and generate the one or more evidence predictions based on one or more weights trained on the one or more categorical identifier-evidence text portion pairs and ground truth data comprising one or more model-generated training labels or one or more expert-labeled document data objects.

18. The one or more non-transitory computer-readable storage media of claim 16, further including instructions that, when executed by the one or more processors, cause the one or more processors to:

receive a plurality of categorical identifier-evidence text portion pairs, the plurality of categorical identifier-evidence text portion pairs comprising the plurality of evidence text portions and a plurality of candidate categorical identifiers;

generate a plurality of evidence scores for respective ones of the plurality of categorical identifier-evidence text portion pairs; and determine whether the plurality of model-assigned categorical identifiers are correctly assigned to the plurality of text segment data objects based on the plurality of evidence scores.

19. The one or more non-transitory computer-readable storage media of claim 16, further including instructions that, when executed by the one or more processors, cause the one or more processors to:

determine one or more loss values based on a difference between the one or more evidence predictions and one or more model-generated training labels or one or more expert-labeled document data objects; and generate one or more weights associated with the second machine learning model based on the loss value.

20. The one or more non-transitory computer-readable storage media of claim 16, further including instructions that, when executed by the one or more processors, cause the one or more processors to:

generate a plurality of prediction loss values by (a) normalizing the plurality of evidence predictions and (b) determining a cross-entropy of the normalized plurality of evidence predictions;

generate a plurality of confidence scores by row max pooling the plurality of evidence predictions;

generate a plurality of weights by normalizing the plurality of confidence scores;

generate a categorical identifier loss value comprising a sum based on the plurality of prediction loss values and the plurality of weights;

validate the plurality of confidence scores with ground truth data;

generate an evidence loss value by (a) normalizing the validated plurality of confidence scores and (b) determining a binary cross-entropy of the normalized and validated plurality of confidence scores; and generate a total loss value based on the categorical identifier loss value and the evidence loss value.

* * * * *